(12) United States Patent
Endou et al.

(10) Patent No.: US 7,419,790 B2
(45) Date of Patent: Sep. 2, 2008

(54) SODIUM-INDEPENDENT TRANSPORTER CARRYING ACIDIC AMINO ACID AND ITS GENE

(75) Inventors: Hitoshi Endou, Kanagawa (JP); Yoshikatsu Kanai, Tokyo (JP)

(73) Assignee: J-Pharma Co., Ltd, Tokyo (JP)

( * ) Notice: Subject to any disclaimer, the term of this patent is extended or adjusted under 35 U.S.C. 154(b) by 491 days.

(21) Appl. No.: 10/921,772

(22) Filed: Aug. 18, 2004

(65) Prior Publication Data

US 2005/0069980 A1  Mar. 31, 2005

Related U.S. Application Data

(63) Continuation of application No. PCT/JP03/01614, filed on Feb. 17, 2003.

(30) Foreign Application Priority Data

Feb. 18, 2002 (JP) .............................. 2002-040608

(51) Int. Cl.
*G01N 33/53* (2006.01)
*G01N 33/566* (2006.01)
*C07K 14/00* (2006.01)

(52) U.S. Cl. .................... 435/7.1; 435/7.2; 436/501; 530/350

(58) Field of Classification Search .................. None
See application file for complete search history.

(56) References Cited

FOREIGN PATENT DOCUMENTS

| EP | 1 111 048 A2 | 6/2001 |
|---|---|---|
| WO | WO 01/12660 A2 | 2/2001 |

OTHER PUBLICATIONS

A Chairoungdua et al., "Journ. of Biol. Chem.", vol. 274, No. 41, pp. 28845-28848, 1999.
H. Sato et al., "Journ. of Biol. Chem.", vol. 274, No. 17, pp. 11455-11458, 1999.
H. Matsuo et al., "Journ. of Biol. Chem.", vol. 277, No. 23, pp. 21017-21026, 2002.
Jean-Paul Blondeau, "Gene", vol. 286, pp. 241-248, 2002.
A. Chairoungdua et al., The Journ. of Biol. Chem., vol. 276, No. 52, pp. 49390-49399 (2001).
Database UniProt: XP-002359052 (Dec. 1, 2001).
Database EMBL: XP002359053 (Oct. 8, 2001).

*Primary Examiner*—Elizabeth C. Kemmerer
*Assistant Examiner*—Sandra Wegert
(74) *Attorney, Agent, or Firm*—Peter F. Corless; Christine C. O'Day; Edwards Angell Palmer & Dodge LLP

(57) ABSTRACT

It is intended to provide a sodium-independent transporter carrying an acidic amino acid and its gene. A protein having the amino acid sequence represented by SEQ ID NO: 1 and being capable of sodium-independently transporting an acidic amino acid and its analogs; a gene encoding this protein; a fused protein of the above protein with an auxiliary factor enabling the expression of its function; a gene encoding the same; a method of analyzing the function of a transporter using the same: and utilization thereof.

2 Claims, 13 Drawing Sheets

FIG. 1

AGT1

4F2hc
rBAT

AGT1-4F2hc fusion protein

| AGT1 | | 4F2hc |
|---|---|---|
| GAA GAA AGT | GCG GCC GCA | AGC CAG GAC |
| E   E   S | A   A   A | S   Q   D |

AGT1-rBAT fusion protein

| AGT1 | | rBAT |
|---|---|---|
| GAA GAA AGT | GCG GCC GCA | GAT GAG GAC |
| E   E   S | A   A   A | D   E   D |

SEQUENCE LISTING

<160> NUMBER OF SEQ ID NOS: 22

<210> SEQ ID NO 1
<211> LENGTH: 478
<212> TYPE: PRT
<213> ORGANISM: Mus sp.
<220> FEATURE:
<223> OTHER INFORMATION: AGT1

<400> SEQUENCE: 1

```
Met Ala Met Asp Ser Lys Lys Glu Ile Arg Leu Lys Arg Glu Leu Gly
 1               5                  10                  15

Tyr Phe Trp Gly Thr Asn Phe Leu Ile Ile Asn Ile Ile Gly Ala Gly
                20                  25                  30

Ile Phe Val Ser Pro Lys Gly Val Leu Gln His Ser Ser Met Asn Val
            35                  40                  45

Gly Val Ser Leu Cys Val Trp Ala Val Cys Ala Val Leu Thr Leu Thr
        50                  55                  60

Ser Ala Leu Cys Ser Ala Glu Ile Gly Ile Thr Phe Pro Tyr Ser Gly
 65                  70                  75                  80

Ala His Tyr Tyr Phe Leu Lys Arg Cys Phe Gly Pro Leu Val Ala Phe
                85                  90                  95

Leu Arg Leu Trp Thr Ser Leu Phe Leu Gly Pro Gly Leu Ile Ala Ser
                100                 105                 110

Gln Ala Leu Leu Leu Ala Glu Tyr Gly Val Gln Pro Phe Tyr Pro Ser
            115                 120                 125

Cys Ser Ala Pro Ile Leu Pro Arg Lys Cys Leu Ala Leu Ala Met Leu
        130                 135                 140

Trp Ile Val Gly Ile Leu Asn Ser Arg Gly Val Lys Glu Leu Ser Trp
145                 150                 155                 160

Leu Gln Thr Val Ser Ser Val Leu Lys Val Gly Ile Leu Gly Val Ile
                165                 170                 175

Ser Leu Ser Gly Leu Phe Leu Leu Val Arg Gly Lys Lys Glu Asn Val
                180                 185                 190

Gln Arg Leu Gln Asn Ala Phe Asp Ala Glu Phe Pro Glu Val Ser Gln
            195                 200                 205

Leu Ile Glu Ala Ile Phe Gln Gly Tyr Phe Ala Phe Ser Gly Gly Gly
        210                 215                 220

Cys Phe Thr Cys Ile Ala Gly Glu Leu Lys Lys Pro Ser Lys Thr Ile
225                 230                 235                 240

Pro Arg Cys Ile Phe Thr Gly Leu Pro Leu Val Thr Val Val Tyr Leu
                245                 250                 255
```

```
Leu Ala Asn Ile Ser Tyr Leu Thr Val Leu Thr Pro Gln Glu Met Leu
            260                 265                 270

Ser Ser Asp Ala Val Ala Leu Thr Trp Thr Asp Arg Val Ile Pro Gln
            275                 280                 285

Phe Thr Trp Thr Val Pro Phe Ala Ile Ser Ala Ser Leu Phe Ile Asn
            290                 295                 300

Leu Val Ile Asn Val Leu Glu Thr Ser Arg Val Leu Tyr Ile Ala Ser
305                 310                 315                 320

Glu Asn Gly Gln Leu Pro Leu Leu Phe Cys Ala Leu Asn Val His Ser
                325                 330                 335

Ser Pro Phe Ile Ala Val Leu Leu Ile Ile Ser Met Ala Ser Ile Leu
            340                 345                 350

Ile Val Leu Thr Asn Leu Ile Asp Leu Ile Asn Tyr Leu Tyr Phe Val
            355                 360                 365

Val Ser Ile Trp Thr Ala Leu Ser Ile Ile Gly Ile Leu Lys Leu Arg
            370                 375                 380

Tyr Gln Glu Pro Asn Leu His Arg Pro Tyr Lys Val Phe Leu Pro Phe
385                 390                 395                 400

Thr Phe Ile Ala Leu Gly Ile Thr Leu Ser Leu Val Leu Ile Pro Leu
                405                 410                 415

Val Lys Ser Pro Lys Leu His Tyr Ile Tyr Val Phe Leu Phe Leu Leu
            420                 425                 430

Ser Gly Leu Val Phe Tyr Val Pro Leu Ile His Phe Lys Val Lys Phe
            435                 440                 445

Val Trp Phe Gln Lys Leu Thr Cys Tyr Leu Gln Leu Leu Phe Asn Ile
            450                 455                 460

Cys Ile Pro Asp Val Ser Asp Asp His Ile His Glu Glu Ser
465                 470                 475

<210> SEQ ID NO 2
<211> LENGTH: 2141
<212> TYPE: DNA
<213> ORGANISM: Mus sp.
<220> FEATURE:
<221> NAME/KEY: CDS
<222> LOCATION: (59)..(1492)
<220> FEATURE:
<223> OTHER INFORMATION: AGT1

<400> SEQUENCE: 2
caaacctata ggcagaaaca ttcacagagt acaattttgt gaatgtaaac ttctctca         58 atg gca atg gat tca aag aag gaa atc cgt ctt aag aga gaa ctt gga       106
Met Ala Met Asp Ser Lys Lys Glu Ile Arg Leu Lys Arg Glu Leu Gly
  1               5                  10                  15 tat ttc tgg ggg aca aac ttt tta att att aat ata att ggt gca gga       154
Tyr Phe Trp Gly Thr Asn Phe Leu Ile Ile Asn Ile Ile Gly Ala Gly
             20                  25                  30 ata ttt gtg tcc ccc aag gga gtg ctc cag cac tct tcc atg aat gtt       202
Ile Phe Val Ser Pro Lys Gly Val Leu Gln His Ser Ser Met Asn Val
         35                  40                  45 gga gtc tcc ttg tgt gtt tgg gct gtc tgt gca gtg ctg acc ttg acc       250
Gly Val Ser Leu Cys Val Trp Ala Val Cys Ala Val Leu Thr Leu Thr
     50                  55                  60 agt gct ctc tgc tct gca gag atc ggg ata acc ttc cca tac agt ggg       298
Ser Ala Leu Cys Ser Ala Glu Ile Gly Ile Thr Phe Pro Tyr Ser Gly
 65                  70                  75                  80 gct cac tat tat ttt tta aag cga tgc ttc ggc cct ctc gtg gca ttc       346
Ala His Tyr Tyr Phe Leu Lys Arg Cys Phe Gly Pro Leu Val Ala Phe
```

-continued

```
                   85                   90                   95
ctg agg ctt tgg act agc ttg ttt ctc ggc cca ggc tta att gct agc      394
Leu Arg Leu Trp Thr Ser Leu Phe Leu Gly Pro Gly Leu Ile Ala Ser
            100                 105                 110 caa gct ctg cta ctg gct gag tat ggc gtt cag cct ttt tat ccc agc      442
Gln Ala Leu Leu Leu Ala Glu Tyr Gly Val Gln Pro Phe Tyr Pro Ser
            115                 120                 125 tgc tct gcc ccg att cta cca aga aaa tgt ctg gcc ctg gcg atg ctg      490
Cys Ser Ala Pro Ile Leu Pro Arg Lys Cys Leu Ala Leu Ala Met Leu
130                 135                 140 tgg att gtg gga att ctg aat tct cgt ggt gta aaa gag ctg tca tgg      538
Trp Ile Val Gly Ile Leu Asn Ser Arg Gly Val Lys Glu Leu Ser Trp
145                 150                 155                 160 ctt cag aca gtg agc tca gtg ctg aag gtg ggc ata ctc ggt gtc att      586
Leu Gln Thr Val Ser Ser Val Leu Lys Val Gly Ile Leu Gly Val Ile
            165                 170                 175 tcc ctc agc ggc ctg ttc ttg ctg gtg aga ggg aag aag gag aat gta      634
Ser Leu Ser Gly Leu Phe Leu Leu Val Arg Gly Lys Lys Glu Asn Val
            180                 185                 190 caa agg ctt cag aat gcg ttt gat gcc gag ttc cca gag gtc tct cag      682
Gln Arg Leu Gln Asn Ala Phe Asp Ala Glu Phe Pro Glu Val Ser Gln
            195                 200                 205 tta ata gaa gct att ttc caa gga tac ttt gcg ttt tct ggc ggg gga      730
Leu Ile Glu Ala Ile Phe Gln Gly Tyr Phe Ala Phe Ser Gly Gly Gly
210                 215                 220 tgc ttt aca tgt ata gca ggg gag ctg aag aaa ccc agt aaa aca att      778
Cys Phe Thr Cys Ile Ala Gly Glu Leu Lys Lys Pro Ser Lys Thr Ile
225                 230                 235                 240 cct aga tgc atc ttt aca gga ctg cct ctg gta act gtc gtg tac tta      826
Pro Arg Cys Ile Phe Thr Gly Leu Pro Leu Val Thr Val Val Tyr Leu
            245                 250                 255 ctg gct aat att tcc tac ctg aca gtt ctg aca ccc cag gaa atg ctc      874
Leu Ala Asn Ile Ser Tyr Leu Thr Val Leu Thr Pro Gln Glu Met Leu
            260                 265                 270 tct tca gat gct gtt gct ctt aca tgg aca gac agg gtc att ccc caa      922
Ser Ser Asp Ala Val Ala Leu Thr Trp Thr Asp Arg Val Ile Pro Gln
            275                 280                 285 ttc aca tgg act gtt cct ttt gct att tct gct tca ctg ttt atc aac      970
Phe Thr Trp Thr Val Pro Phe Ala Ile Ser Ala Ser Leu Phe Ile Asn
            290                 295                 300 ctt gtg att aat gta ctt gag aca tca aga gtg tta tat att gca agt      1018
Leu Val Ile Asn Val Leu Glu Thr Ser Arg Val Leu Tyr Ile Ala Ser
305                 310                 315                 320 gag aat ggc cag ctg cct ttg ttg ttt tgt gcc ctg aat gtc cat tcc      1066
Glu Asn Gly Gln Leu Pro Leu Leu Phe Cys Ala Leu Asn Val His Ser
            325                 330                 335 tct ccc ttt ata gct gtg cta cta att atc agt atg gca tcc att tta      1114
Ser Pro Phe Ile Ala Val Leu Leu Ile Ile Ser Met Ala Ser Ile Leu
            340                 345                 350 att gtc tta aca aac cta att gat ctg ata aac tat ctc tat ttt gtt      1162
Ile Val Leu Thr Asn Leu Ile Asp Leu Ile Asn Tyr Leu Tyr Phe Val
            355                 360                 365 gtt tcc att tgg act gcc tta tca ata ata gga atc ttg aaa ctg agg      1210
Val Ser Ile Trp Thr Ala Leu Ser Ile Ile Gly Ile Leu Lys Leu Arg
370                 375                 380 tac caa gag ccc aat cta cac aga cca tat aag gtg ttt tta ccg ttc      1258
Tyr Gln Glu Pro Asn Leu His Arg Pro Tyr Lys Val Phe Leu Pro Phe
385                 390                 395                 400 aca ttc ata gcg ttg ggc atc acc ctg agc ttg gtt ttg atc ccg ctt      1306
```

-continued

```
Thr Phe Ile Ala Leu Gly Ile Thr Leu Ser Leu Val Leu Ile Pro Leu
            405                 410                 415 gtc aag tct cca aag ttg cat tat atc tat gtg ttc ctc ttc ctt ctc    1354
Val Lys Ser Pro Lys Leu His Tyr Ile Tyr Val Phe Leu Phe Leu Leu
            420                 425                 430 agt ggg ctg gtg ttt tac gtg cca ttg ata cac ttt aaa gtg aag ttc    1402
Ser Gly Leu Val Phe Tyr Val Pro Leu Ile His Phe Lys Val Lys Phe
            435                 440                 445 gtt tgg ttt cag aag ttg act tgc tat ctg cag tta ctg ttt aat att    1450
Val Trp Phe Gln Lys Leu Thr Cys Tyr Leu Gln Leu Leu Phe Asn Ile
            450                 455                 460 tgc atc cct gat gtg tct gat gac cac ata cat gaa gaa agt            1492
Cys Ile Pro Asp Val Ser Asp Asp His Ile His Glu Glu Ser
465                 470                 475 tgaggaagaa tagcctttgt agccatactg tgttccagat aaaggttaag tgtaagctaa    1552
aatagtaatg atggcaatgc tataaactga aatggtatat agaaaagtac ccaggaaatt    1612
cctagttttt aaaatatcaa aggaaatggc tgggtagatg actgtgctgt taagggcacc    1672
agatgtcctt ccaggggact gaagttcaat tcacaggccc cacttagaag ttcataacta    1732
tctgtaattc tagtcacaga ggatccaata tcctctactg gattctacca gcactgcatg    1792
catctggagt agagacatac atgtaggcac ccatgcacat ttacaagaag aaagaaagag    1852
agaaagaaag aaagaaagaa agaaagaaag aaagaaagaa agaaagaaag aaagggagag    1912
ggagagagga aggaaggaag gaaataagga agaaggaag gaggaaagaa agacagtaaa    1972
gaaagtattt cacataacta aactgttttt attaaaaata aaatttctag cttgtatagc    2032
ttcatgtagt aagaatatct ttctcattct tctgtttatc tcatcgattt tctactgaat    2092
gtattcttat aataaaagtt actgatggaa attaaaaaaa aaaaaaaaa                2141
```

<210> SEQ ID NO 3
<211> LENGTH: 526
<212> TYPE: PRT
<213> ORGANISM: Mus sp.
<220> FEATURE:
<223> OTHER INFORMATION: 4F2hc

<400> SEQUENCE: 3

```
Met Ser Gln Asp Thr Glu Val Asp Met Lys Asp Val Glu Leu Asn Glu
 1               5                  10                  15

Leu Glu Pro Glu Lys Gln Pro Met Asn Ala Ala Asp Gly Ala Ala Ala
            20                  25                  30

Gly Glu Lys Asn Gly Leu Val Lys Ile Lys Val Ala Glu Asp Glu Thr
        35                  40                  45

Glu Ala Gly Val Lys Phe Thr Gly Leu Ser Lys Glu Glu Leu Leu Lys
    50                  55                  60

Val Ala Gly Ser Pro Gly Trp Val Arg Thr Arg Trp Ala Leu Leu Leu
65                  70                  75                  80

Leu Phe Trp Leu Gly Trp Leu Gly Met Leu Ala Gly Ala Val Val Ile
                85                  90                  95

Ile Val Arg Ala Pro Arg Cys Arg Glu Leu Pro Val Gln Arg Trp Trp
            100                 105                 110

His Lys Gly Ala Leu Tyr Arg Ile Gly Asp Leu Gln Ala Phe Val Gly
        115                 120                 125

Arg Asp Ala Gly Gly Ile Ala Gly Leu Lys Ser His Leu Glu Tyr Leu
    130                 135                 140

Ser Thr Leu Lys Val Lys Gly Leu Val Leu Gly Pro Ile His Lys Asn
```

-continued

```
            145                 150                 155                 160
Gln Lys Asp Glu Ile Asn Glu Thr Asp Leu Lys Gln Ile Asn Pro Thr
                165                 170                 175

Leu Gly Ser Gln Glu Asp Phe Lys Asp Leu Leu Gln Ser Ala Lys Lys
            180                 185                 190

Lys Ser Ile His Ile Ile Leu Asp Leu Thr Pro Asn Tyr Gln Gly Gln
        195                 200                 205

Asn Ala Trp Phe Leu Pro Ala Gln Ala Asp Ile Val Ala Thr Lys Met
    210                 215                 220

Lys Glu Ala Leu Ser Ser Trp Leu Gln Asp Gly Val Asp Gly Phe Gln
225                 230                 235                 240

Phe Arg Asp Val Gly Lys Leu Met Asn Ala Pro Leu Tyr Leu Ala Glu
                245                 250                 255

Trp Gln Asn Ile Thr Lys Asn Leu Ser Glu Asp Arg Leu Leu Ile Ala
                260                 265                 270

Gly Thr Glu Ser Ser Asp Leu Gln Gln Ile Val Asn Ile Leu Glu Ser
            275                 280                 285

Thr Ser Asp Leu Leu Leu Thr Ser Ser Tyr Leu Ser Asn Ser Thr Phe
        290                 295                 300

Thr Gly Glu Arg Thr Glu Ser Leu Val Thr Arg Phe Leu Asn Ala Thr
305                 310                 315                 320

Gly Ser Gln Trp Cys Ser Trp Ser Val Ser Gln Ala Gly Leu Leu Ala
                325                 330                 335

Asp Phe Ile Pro Asp His Leu Leu Arg Leu Tyr Gln Leu Leu Leu Phe
                340                 345                 350

Thr Leu Pro Gly Thr Pro Val Phe Ser Tyr Gly Asp Glu Leu Gly Leu
            355                 360                 365

Gln Gly Ala Leu Pro Gly Gln Pro Ala Lys Ala Pro Leu Met Pro Trp
        370                 375                 380

Asn Glu Ser Ser Ile Phe His Ile Pro Arg Pro Val Ser Leu Asn Met
385                 390                 395                 400

Thr Val Lys Gly Gln Asn Glu Asp Pro Gly Ser Leu Leu Thr Gln Phe
                405                 410                 415

Arg Arg Leu Ser Asp Leu Arg Gly Lys Glu Arg Ser Leu Leu His Gly
            420                 425                 430

Asp Phe His Ala Leu Ser Ser Ser Pro Asp Leu Phe Ser Tyr Ile Arg
        435                 440                 445

His Trp Asp Gln Asn Glu Arg Tyr Leu Val Val Leu Asn Phe Arg Asp
    450                 455                 460

Ser Gly Arg Ser Ala Arg Leu Gly Ala Ser Asn Leu Pro Ala Gly Ile
465                 470                 475                 480

Ser Leu Pro Ala Ser Ala Lys Leu Leu Leu Ser Thr Asp Ser Ala Arg
                485                 490                 495

Gln Ser Arg Glu Glu Asp Thr Ser Leu Lys Leu Glu Asn Leu Ser Leu
            500                 505                 510

Asn Pro Tyr Glu Gly Leu Leu Leu Gln Phe Pro Phe Val Ala
        515                 520                 525

<210> SEQ ID NO 4
<211> LENGTH: 1852
<212> TYPE: DNA
<213> ORGANISM: Mus sp.
<220> FEATURE:
<221> NAME/KEY: CDS
<222> LOCATION: (106)..(1683)
```

```
<220> FEATURE:
<223> OTHER INFORMATION: 4F2hc

<400> SEQUENCE: 4
gctagcctca cggccacggg acgcctctct gaacggggat ccaggcagga ttagagctgc    60
ctcactgact acaggccgtg tcgtgtcacc gtttctgcag gcacc atg agc cag gac   117
                                                 Met Ser Gln Asp
                                                  1 acc gaa gtg gac atg aaa gat gtg gag ctg aac gag cta gaa ccg gag    165
Thr Glu Val Asp Met Lys Asp Val Glu Leu Asn Glu Leu Glu Pro Glu
  5              10                  15                  20 aag cag ccc atg aat gca gcg gac ggg gcg gcg gcc ggg gag aag aac    213
Lys Gln Pro Met Asn Ala Ala Asp Gly Ala Ala Ala Gly Glu Lys Asn
             25                  30                  35 ggt ctg gtg aag atc aag gtg gcg gag gac gag acg gag gcc ggg gtc    261
Gly Leu Val Lys Ile Lys Val Ala Glu Asp Glu Thr Glu Ala Gly Val
         40                  45                  50 aag ttc acc ggc tta tcc aag gag gag cta ctg aag gta gcg ggc agc    309
Lys Phe Thr Gly Leu Ser Lys Glu Glu Leu Leu Lys Val Ala Gly Ser
     55                  60                  65 cct ggc tgg gtg cgc acc cgc tgg gcg ctg ctg ctc ttc tgg ctc       357
Pro Gly Trp Val Arg Thr Arg Trp Ala Leu Leu Leu Leu Phe Trp Leu
 70                  75                  80 ggt tgg ctg ggc atg ctg gcg ggc gcc gtg gtt atc atc gtt cgg gcg    405
Gly Trp Leu Gly Met Leu Ala Gly Ala Val Val Ile Ile Val Arg Ala
 85                  90                  95                 100 ccg cgc tgc cgt gag ctg cct gta cag agg tgg tgg cac aag ggc gcc    453
Pro Arg Cys Arg Glu Leu Pro Val Gln Arg Trp Trp His Lys Gly Ala
                 105                 110                 115 ctc tac cgc atc ggc gac ctt cag gcc ttt gta ggc cgg gat gcg gga    501
Leu Tyr Arg Ile Gly Asp Leu Gln Ala Phe Val Gly Arg Asp Ala Gly
             120                 125                 130 ggc ata gct ggt ctg aag agc cat ctg gag tac ttg agc acc ctg aag    549
Gly Ile Ala Gly Leu Lys Ser His Leu Glu Tyr Leu Ser Thr Leu Lys
         135                 140                 145 gtg aag ggc ctg gtg tta ggc cca att cac aag aac cag aag gat gaa    597
Val Lys Gly Leu Val Leu Gly Pro Ile His Lys Asn Gln Lys Asp Glu
150                 155                 160 atc aat gaa acc gac ctg aaa cag att aat ccc act ttg ggc tcc cag    645
Ile Asn Glu Thr Asp Leu Lys Gln Ile Asn Pro Thr Leu Gly Ser Gln
165                 170                 175                 180 gaa gat ttt aaa gac ctt cta caa agt gcc aag aaa aag agc att cac    693
Glu Asp Phe Lys Asp Leu Leu Gln Ser Ala Lys Lys Lys Ser Ile His
                 185                 190                 195 atc att ttg gac ctc act ccc aac tac cag ggc cag aat gcg tgg ttc    741
Ile Ile Leu Asp Leu Thr Pro Asn Tyr Gln Gly Gln Asn Ala Trp Phe
             200                 205                 210 ctc cct gct cag gct gac att gta gcc acc aaa atg aag gaa gct ctg    789
Leu Pro Ala Gln Ala Asp Ile Val Ala Thr Lys Met Lys Glu Ala Leu
         215                 220                 225 agt tct tgg ttg cag gac ggt gtg gat ggt ttc caa ttc cgg gat gtg    837
Ser Ser Trp Leu Gln Asp Gly Val Asp Gly Phe Gln Phe Arg Asp Val
     230                 235                 240 gga aag ctg atg aat gca ccc ttg tac ttg gct gag tgg cag aat atc    885
Gly Lys Leu Met Asn Ala Pro Leu Tyr Leu Ala Glu Trp Gln Asn Ile
245                 250                 255                 260 acc aag aac tta agt gag gac agg ctt ttg att gca ggg act gag tcc    933
Thr Lys Asn Leu Ser Glu Asp Arg Leu Leu Ile Ala Gly Thr Glu Ser
                 265                 270                 275
```

```
tct gac ctg cag caa att gtc aac ata ctt gaa tcc acc agc gac ctg      981
Ser Asp Leu Gln Gln Ile Val Asn Ile Leu Glu Ser Thr Ser Asp Leu
            280                 285                 290 ctg ttg acc agc tcc tac ctg tca aat tcc act ttc act ggg gag cgt     1029
Leu Leu Thr Ser Ser Tyr Leu Ser Asn Ser Thr Phe Thr Gly Glu Arg
        295                 300                 305 act gaa tcc cta gtc act agg ttt ttg aat gcc act ggc agc caa tgg     1077
Thr Glu Ser Leu Val Thr Arg Phe Leu Asn Ala Thr Gly Ser Gln Trp
310                 315                 320 tgc agc tgg agt gtg tcg caa gca gga ctc ctc gca gac ttt ata ccg     1125
Cys Ser Trp Ser Val Ser Gln Ala Gly Leu Leu Ala Asp Phe Ile Pro
325                 330                 335                 340 gac cat ctt ctc cga ctc tac cag ctg ctg ctc ttc act ctg cca ggg     1173
Asp His Leu Leu Arg Leu Tyr Gln Leu Leu Leu Phe Thr Leu Pro Gly
            345                 350                 355 act cct gtt ttt agc tac ggg gat gag ctt ggc ctt cag ggt gcc ctt     1221
Thr Pro Val Phe Ser Tyr Gly Asp Glu Leu Gly Leu Gln Gly Ala Leu
        360                 365                 370 cct gga cag cct gcg aag gcc cca ctc atg ccg tgg aat gag tcc agc     1269
Pro Gly Gln Pro Ala Lys Ala Pro Leu Met Pro Trp Asn Glu Ser Ser
    375                 380                 385 atc ttt cac atc cca aga cct gta agc ctc aac atg aca gtg aag ggc     1317
Ile Phe His Ile Pro Arg Pro Val Ser Leu Asn Met Thr Val Lys Gly
390                 395                 400 cag aat gaa gac cct ggc tcc ctt ctt acc cag ttc cgg cgg ctg agt     1365
Gln Asn Glu Asp Pro Gly Ser Leu Leu Thr Gln Phe Arg Arg Leu Ser
405                 410                 415                 420 gac ctt cgg ggt aag gag cgc tct ctg ttg cac ggt gac ttc cat gca     1413
Asp Leu Arg Gly Lys Glu Arg Ser Leu Leu His Gly Asp Phe His Ala
            425                 430                 435 ctg tct tcc tca cct gac ctc ttc tcc tac ata cga cac tgg gac cag     1461
Leu Ser Ser Ser Pro Asp Leu Phe Ser Tyr Ile Arg His Trp Asp Gln
        440                 445                 450 aat gag cgt tac ctg gtg gtg ctc aac ttc cga gat tcg ggc cgg tca     1509
Asn Glu Arg Tyr Leu Val Val Leu Asn Phe Arg Asp Ser Gly Arg Ser
    455                 460                 465 gcc agg cta ggg gcc tcc aac ctc cct gct ggc ata agc ctg cca gcc     1557
Ala Arg Leu Gly Ala Ser Asn Leu Pro Ala Gly Ile Ser Leu Pro Ala
470                 475                 480 agc gct aaa ctt ttg ctt agt acc gac agt gcc cgg caa agc cgt gag     1605
Ser Ala Lys Leu Leu Leu Ser Thr Asp Ser Ala Arg Gln Ser Arg Glu
485                 490                 495                 500 gag gac acc tcc ctg aag ctg gaa aac ctg agc ctg aat cct tat gag     1653
Glu Asp Thr Ser Leu Lys Leu Glu Asn Leu Ser Leu Asn Pro Tyr Glu
            505                 510                 515 ggc ttg ctg tta cag ttc ccc ttt gtg gcc tgatccttcc tatgcagaac       1703
Gly Leu Leu Leu Gln Phe Pro Phe Val Ala
        520                 525 ctaccaccct cctttgttct ccccaggcct tttggattct agtcttcctc tccttgtttt   1763 taaactttg cagattacat acgaattctt atactgggtg tttttgtctt caaataaaaa    1823
catcacccct gcctcaaaaa aaaaaaaaa                                     1852

<210> SEQ ID NO 5
<211> LENGTH: 685
<212> TYPE: PRT
<213> ORGANISM: Mus sp.
<220> FEATURE:
<223> OTHER INFORMATION: rBAT

<400> SEQUENCE: 5
```

```
Met Asp Glu Asp Lys Gly Lys Arg Asp Pro Ile Gln Met Ser Met Lys
 1               5                  10                  15

Gly Cys Arg Thr Asn Asn Gly Phe Val Gln Asn Glu Asp Ile Pro Glu
                20                  25                  30

Gln Asp Pro Asp Pro Gly Ser Arg Asp Thr Pro Gln Pro Asn Ala Val
                35                  40                  45

Ser Ile Pro Ala Pro Glu Pro His Leu Lys Ala Val Arg Pro Tyr
         50                  55                  60

Ala Gly Met Pro Lys Glu Val Leu Phe Gln Phe Ser Gly Gln Ala Arg
 65                  70                  75                  80

Tyr Arg Val Pro Arg Glu Ile Leu Phe Trp Leu Thr Val Val Ser Val
                 85                  90                  95

Phe Leu Leu Ile Gly Ala Thr Ile Ala Ile Val Ile Ser Pro Lys
                100                 105                 110

Cys Leu Asp Trp Trp Gln Ala Gly Pro Ile Tyr Gln Ile Tyr Pro Arg
            115                 120                 125

Ser Phe Lys Asp Ser Asp Lys Asp Gly Asn Gly Asp Leu Lys Gly Ile
        130                 135                 140

Gln Glu Lys Leu Asp Tyr Ile Thr Ala Leu Asn Ile Lys Thr Leu Trp
145                 150                 155                 160

Ile Thr Ser Phe Tyr Lys Ser Ile Phe Glu Asp Phe Arg Tyr Ala Val
                165                 170                 175

Glu Asp Ile Lys Glu Ile Asp Pro Ile Phe Gly Thr Met Lys Asp Phe
            180                 185                 190

Glu Asn Leu Val Ala Ala Ile His Asp Lys Gly Leu Lys Leu Ile Ile
        195                 200                 205

Asp Phe Ile Pro Asn His Thr Ser Asp Lys His Pro Trp Phe Gln Ser
    210                 215                 220

Ser Arg Thr Arg Ser Gly Lys Tyr Thr Asp Tyr Tyr Ile Trp His Asn
225                 230                 235                 240

Cys Thr His Cys Gln Arg Val Pro Thr Pro Asn Asn Trp Leu Ser
                245                 250                 255

Val Tyr Gly His Ser Ser Trp His Phe Asp Glu Val Arg Glu Gln Cys
            260                 265                 270

Tyr Phe His Gln Phe Leu Arg Glu Gln Pro Asp Leu Tyr Phe Arg Asn
        275                 280                 285

Pro Ala Val Gln Glu Glu Ile Lys Glu Ile Ile Thr Phe Trp Leu Ser
    290                 295                 300

Lys Gly Val Asp Gly Phe Ser Phe Asp Ala Val Lys Phe Leu Leu Glu
305                 310                 315                 320

Ala Lys Asp Leu Arg Asn Glu Ile Gln Val Asn Thr Ser Gln Ile Pro
                325                 330                 335

Asp Thr Val Thr His Tyr Ser Glu Leu Tyr His Asp Phe Thr Thr Thr
            340                 345                 350

Gln Val Gly Met His Asp Ile Val Arg Asp Phe Arg Gln Thr Met Asn
        355                 360                 365

Gln Tyr Ser Arg Glu Pro Gly Arg Tyr Arg Phe Met Gly Ala Glu Ala
    370                 375                 380

Ser Ala Glu Ser Ile Glu Arg Thr Met Met Tyr Tyr Gly Leu Pro Phe
385                 390                 395                 400

Ile Gln Glu Ala Asp Phe Pro Phe Asn Lys Tyr Phe Thr Thr Ile Gly
                405                 410                 415
```

```
Thr Leu Ser Gly His Thr Val Tyr Glu Val Ile Thr Ser Trp Met Glu
            420                 425                 430

Asn Met Pro Glu Gly Lys Trp Pro Asn Trp Met Thr Gly Gly Pro Glu
            435                 440                 445

Thr Pro Arg Leu Thr Ser Arg Val Gly Ser Glu Tyr Val Asn Ala Met
            450                 455                 460

His Met Leu Leu Phe Thr Leu Pro Gly Thr Pro Ile Thr Tyr Tyr Gly
465                 470                 475                 480

Glu Glu Ile Gly Met Gly Asp Ile Ser Val Thr Asn Phe Asn Glu Ser
            485                 490                 495

Tyr Asp Ser Thr Thr Leu Val Ser Lys Ser Pro Met Gln Trp Asp Asn
            500                 505                 510

Ser Ser Asn Ala Gly Phe Thr Glu Ala Asn His Thr Trp Leu Pro Pro
            515                 520                 525

Asn Ser Asp Tyr His Thr Val Asn Val Asp Val Gln Lys Thr Gln Pro
            530                 535                 540

Ser Ser Ala Leu Arg Leu Tyr Gln Asp Leu Ser Leu Leu His Ala Thr
545                 550                 555                 560

Glu Leu Val Leu Ser Arg Gly Trp Phe Cys Leu Leu Arg Asp Asp Ser
            565                 570                 575

His Ser Val Val Tyr Thr Arg Glu Leu Asp Gly Ile Asp Asn Val Phe
            580                 585                 590

Leu Val Val Leu Asn Phe Gly Glu Ser Ser Thr Val Leu Asn Leu Gln
            595                 600                 605

Gly Ile Ile Ser Asp Leu Pro Pro Glu Leu Arg Ile Arg Leu Ser Thr
            610                 615                 620

Asn Ser Ala Ser Lys Gly Ser Ala Val Asp Thr Arg Ala Ile Ser Leu
625                 630                 635                 640

Glu Lys Gly Glu Gly Leu Val Leu Glu His Ser Thr Lys Ala Pro Leu
            645                 650                 655

His Gln Gln Ala Ala Phe Arg Asp Arg Cys Phe Val Ser Ser Arg Ala
            660                 665                 670

Cys Tyr Ser Ser Ala Leu Asp Ile Leu Tyr Ser Ser Cys
            675                 680                 685

<210> SEQ ID NO 6
<211> LENGTH: 2287
<212> TYPE: DNA
<213> ORGANISM: Mus sp.
<220> FEATURE:
<221> NAME/KEY: CDS
<222> LOCATION: (46)..(2100)
<220> FEATURE:
<223> OTHER INFORMATION: rBAT

<400> SEQUENCE: 6
gatccccctg ctggaaagca ccaggaagag ctacacaggg tagac atg gat gag gac      57
                                                Met Asp Glu Asp
                                                  1 aaa ggc aag aga gac ccc atc caa atg agt atg aag gga tgc cga acc      105
Lys Gly Lys Arg Asp Pro Ile Gln Met Ser Met Lys Gly Cys Arg Thr
  5                  10                  15                  20 aat aac ggg ttt gtc caa aat gaa gac att ccg gag cag gac cca gac      153
Asn Asn Gly Phe Val Gln Asn Glu Asp Ile Pro Glu Gln Asp Pro Asp
                 25                  30                  35 cca ggc tcc agg gac acc cca cag ccc aac gcc gtg agt atc cct gct      201
Pro Gly Ser Arg Asp Thr Pro Gln Pro Asn Ala Val Ser Ile Pro Ala
         40                  45                  50
```

-continued

```
cca gag gag cct cac cta aag gcg gtg cgg ccc tat gca ggg atg ccc      249
Pro Glu Glu Pro His Leu Lys Ala Val Arg Pro Tyr Ala Gly Met Pro
            55                  60                  65 aag gaa gta ctc ttc cag ttc tcc ggc cag gct cgc tac cgg gtg ccc      297
Lys Glu Val Leu Phe Gln Phe Ser Gly Gln Ala Arg Tyr Arg Val Pro
    70                  75                  80 cga gag atc ctc ttc tgg ctc acc gtg gtt tcc gtg ttc ctc att          345
Arg Glu Ile Leu Phe Trp Leu Thr Val Val Ser Val Phe Leu Leu Ile
85                  90                  95                 100 gga gcc acc ata gcc atc atc gtc atc tct cca aaa tgc ctt gac tgg      393
Gly Ala Thr Ile Ala Ile Ile Val Ile Ser Pro Lys Cys Leu Asp Trp
                105                 110                 115 tgg caa gca ggt ccc ata tac cag atc tac ccg agg tct ttt aag gac      441
Trp Gln Ala Gly Pro Ile Tyr Gln Ile Tyr Pro Arg Ser Phe Lys Asp
        120                 125                 130 agt gac aag gat ggg aat gga gac ctg aaa ggt atc cag gag aag ctg      489
Ser Asp Lys Asp Gly Asn Gly Asp Leu Lys Gly Ile Gln Glu Lys Leu
    135                 140                 145 gac tat atc act gct tta aac ata aag act ctt tgg atc act tcc ttt      537
Asp Tyr Ile Thr Ala Leu Asn Ile Lys Thr Leu Trp Ile Thr Ser Phe
150                 155                 160 tat aaa tcg atc ttt gaa gac ttc aga tac gct gtt gag gat atc aaa      585
Tyr Lys Ser Ile Phe Glu Asp Phe Arg Tyr Ala Val Glu Asp Ile Lys
165                 170                 175                 180 gaa att gac cct att ttt gga aca atg aaa gat ttt gag aat ttg gtt      633
Glu Ile Asp Pro Ile Phe Gly Thr Met Lys Asp Phe Glu Asn Leu Val
                185                 190                 195 gct gcc atc cat gac aaa ggt tta aaa tta ata att gat ttc ata cca      681
Ala Ala Ile His Asp Lys Gly Leu Lys Leu Ile Ile Asp Phe Ile Pro
            200                 205                 210 aac cac act agt gac aaa cat cct tgg ttc caa tcg agt agg aca cgg      729
Asn His Thr Ser Asp Lys His Pro Trp Phe Gln Ser Ser Arg Thr Arg
        215                 220                 225 agc gga aaa tac acc gat tac tac atc tgg cac aac tgt acc cat tgt      777
Ser Gly Lys Tyr Thr Asp Tyr Tyr Ile Trp His Asn Cys Thr His Cys
    230                 235                 240 caa cgt gta ccc acc cct ccc aac aac tgg ctg agt gtg tat gga cac      825
Gln Arg Val Pro Thr Pro Pro Asn Asn Trp Leu Ser Val Tyr Gly His
245                 250                 255                 260 tcc agc tgg cac ttt gat gaa gta cga gag caa tgt tat ttt cac cag      873
Ser Ser Trp His Phe Asp Glu Val Arg Glu Gln Cys Tyr Phe His Gln
                265                 270                 275 ttt ttg aga gag caa cca gat tta tat ttc cga aat cct gct gtt caa      921
Phe Leu Arg Glu Gln Pro Asp Leu Tyr Phe Arg Asn Pro Ala Val Gln
            280                 285                 290 gag gaa ata aag gaa ata ata acg ttc tgg ctc tcg aag ggt gtt gat      969
Glu Glu Ile Lys Glu Ile Ile Thr Phe Trp Leu Ser Lys Gly Val Asp
        295                 300                 305 ggg ttt agt ttt gat gca gtt aaa ttt ctt ctg gaa gcg aag gat ctg     1017
Gly Phe Ser Phe Asp Ala Val Lys Phe Leu Leu Glu Ala Lys Asp Leu
    310                 315                 320 aga aat gaa atc caa gtg aat aca tcc caa att ccg gac acg gtc acc     1065
Arg Asn Glu Ile Gln Val Asn Thr Ser Gln Ile Pro Asp Thr Val Thr
325                 330                 335                 340 cac tac tca gag ctg tac cat gac ttc acc aca act cag gtg gga atg     1113
His Tyr Ser Glu Leu Tyr His Asp Phe Thr Thr Thr Gln Val Gly Met
                345                 350                 355 cat gac atc gtc cga gac ttc cgg cag acc atg aac cag tac agc agg     1161
His Asp Ile Val Arg Asp Phe Arg Gln Thr Met Asn Gln Tyr Ser Arg
```

-continued

```
            360                 365                 370
gag cct ggc aga tac cgg ttc atg ggg gcc gaa gcc tca gct gag agc      1209
Glu Pro Gly Arg Tyr Arg Phe Met Gly Ala Glu Ala Ser Ala Glu Ser
        375                 380                 385 atc gag agg acc atg atg tac tat ggc ttg cca ttt atc cag gaa gcc      1257
Ile Glu Arg Thr Met Met Tyr Tyr Gly Leu Pro Phe Ile Gln Glu Ala
390                 395                 400 gac ttt cct ttc aac aag tac ttc acc aca ata ggc act ctc tct ggg      1305
Asp Phe Pro Phe Asn Lys Tyr Phe Thr Thr Ile Gly Thr Leu Ser Gly
405                 410                 415                 420 cat act gtc tat gaa gtt atc aca tcc tgg atg gaa aac atg cct gaa      1353
His Thr Val Tyr Glu Val Ile Thr Ser Trp Met Glu Asn Met Pro Glu
            425                 430                 435 gga aaa tgg ccc aat tgg atg act ggc gga ccg gag act cct cgg ctg      1401
Gly Lys Trp Pro Asn Trp Met Thr Gly Gly Pro Glu Thr Pro Arg Leu
        440                 445                 450 act tct cga gta ggg agt gag tat gtc aac gcc atg cac atg ctc ctg      1449
Thr Ser Arg Val Gly Ser Glu Tyr Val Asn Ala Met His Met Leu Leu
    455                 460                 465 ttc aca ctc ccg gga acg ccc atc act tac tat gga gag gaa atc ggg      1497
Phe Thr Leu Pro Gly Thr Pro Ile Thr Tyr Tyr Gly Glu Glu Ile Gly
470                 475                 480 atg gga gac att tcc gtt aca aat ttc aac gag agc tat gat agt act      1545
Met Gly Asp Ile Ser Val Thr Asn Phe Asn Glu Ser Tyr Asp Ser Thr
485                 490                 495                 500 acc ctt gtc tcc aag tca ccg atg cag tgg gac aat agt tcc aat gct      1593
Thr Leu Val Ser Lys Ser Pro Met Gln Trp Asp Asn Ser Ser Asn Ala
            505                 510                 515 ggg ttt act gag gcc aac cac acc tgg cta cca cca aac tct gac tac      1641
Gly Phe Thr Glu Ala Asn His Thr Trp Leu Pro Pro Asn Ser Asp Tyr
        520                 525                 530 cac acc gtc aat gtg gat gtc caa aag acc cag ccg agc tcc gca ctg      1689
His Thr Val Asn Val Asp Val Gln Lys Thr Gln Pro Ser Ser Ala Leu
    535                 540                 545 agg ctg tat cag gat ctg agt cta ctc cat gcc aca gag ctg gtc ctc      1737
Arg Leu Tyr Gln Asp Leu Ser Leu Leu His Ala Thr Glu Leu Val Leu
550                 555                 560 agc cgg ggc tgg ttt tgc ctc ttg aga gac gac agt cac tct gtg gtg      1785
Ser Arg Gly Trp Phe Cys Leu Leu Arg Asp Asp Ser His Ser Val Val
565                 570                 575                 580 tac aca aga gag ctg gac ggc ata gat aac gtc ttc ctc gtg gtt ctg      1833
Tyr Thr Arg Glu Leu Asp Gly Ile Asp Asn Val Phe Leu Val Val Leu
            585                 590                 595 aat ttt gga gaa tca tca act gtg cta aat cta cag ggg atc att tca      1881
Asn Phe Gly Glu Ser Ser Thr Val Leu Asn Leu Gln Gly Ile Ile Ser
        600                 605                 610 gat ctt cct cca gag ctg aga ata agg tta agt acc aac tca gcc tcc      1929
Asp Leu Pro Pro Glu Leu Arg Ile Arg Leu Ser Thr Asn Ser Ala Ser
    615                 620                 625 aaa ggc agt gct gtt gac acc cgt gcc att tct ctg gag aag gga gag      1977
Lys Gly Ser Ala Val Asp Thr Arg Ala Ile Ser Leu Glu Lys Gly Glu
630                 635                 640 ggc ctg gtc ttg gag cac agc acg aag gct ccc ctc cat cag cag gcc      2025
Gly Leu Val Leu Glu His Ser Thr Lys Ala Pro Leu His Gln Gln Ala
645                 650                 655                 660 gct ttc aga gac aga tgc ttt gtt tcc agt cgg gcg tgc tac tcc agt      2073
Ala Phe Arg Asp Arg Cys Phe Val Ser Ser Arg Ala Cys Tyr Ser Ser
            665                 670                 675 gca ctg gac atc ctc tat agc tcg tgt tagggaggaa gctccctaag           2120
Ala Leu Asp Ile Leu Tyr Ser Ser Cys
```

```
Ala Leu Asp Ile Leu Tyr Ser Ser Cys
        680                 685 agatggccac ccagaacatc acgtacgcac aggctgagca gactcatgaa tggcatcaat    2180
tcttagatat ttctgtagca cgatgcacgt tttttaaagt gtttaaagat tatgccaaat    2240
actaaagcat ttaaatatga aaaaaaaaaa aaaaaagcgg cgcgccg                  2287

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: synthetic
      partial peptide
<220> FEATURE:
<223> OTHER INFORMATION: partial peptide of AGT1(465-478)

<400> SEQUENCE: 7

Cys Ile Pro Asp Val Ser Asp Asp His Ile His Glu Glu Ser
 1               5                  10

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: sense primer for amplification of AGT1

<400> SEQUENCE: 8
gcgcgaagct tacctatagg cagaaacatt c                                     31

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: antisense primer for amplification of AGT1

<400> SEQUENCE: 9
atatgcggcc gcactttctt catgtatgtg gt                                    32

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: sense primer for amplification of rBAT

<400> SEQUENCE: 10
atatgcggcc gcagatgagg acaaaggcaa gag                                   33

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: antisense primer for amplification of rBAT

<400> SEQUENCE: 11
```

-continued gcgcgctcta gaaatgcttt agtatttggc ataatc    36

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: sense primer for amplification of 4F2hc

<400> SEQUENCE: 12
atatgcggcc gcaagccagg acaccgaagt gga    33

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: primer
<220> FEATURE:
<223> OTHER INFORMATION: antisense primer for amplification of 4F2hc

<400> SEQUENCE: 13
gcgctctaga catgaggcag gggtgatgtt tt    32

<210> SEQ ID NO 14
<211> LENGTH: 465
<212> TYPE: PRT
<213> ORGANISM: Mus sp.

<400> SEQUENCE: 14

```
Met Gln Leu Leu Arg Ala Leu Gly Val Phe His Val Ser Met Ile Leu
 1               5                  10                  15

Phe Ser Ala Thr Leu Gly Thr Gly Ile Phe Val Thr Pro Lys Ala Val
                20                  25                  30

Leu Lys Tyr Ser Ser Leu Asn Ile Pro Val Ser Leu Ser Ile Trp Ala
            35                  40                  45

Gly Cys Gly Leu Leu Ser Ile Met Ser Ala Leu Cys Asn Ala Glu Ile
        50                  55                  60

Ala Thr Thr Tyr Pro Leu Ser Gly Ala Ser Tyr Tyr Phe Leu Lys Arg
    65                  70                  75                  80

Thr Leu Gly Ser Ser Val Ala Phe Leu Ser Leu Trp Ile Lys Leu Phe
                85                  90                  95

Ala His Phe Leu Gly Ile Gly Ala Gln Cys Leu Leu Ile Ala Thr Ser
            100                 105                 110

Val Ile Gln Cys Phe Tyr Ser Gly Cys Pro Ala Pro Glu Leu Pro Thr
        115                 120                 125

Lys Cys Leu Ala Leu Ala Ile Leu Trp Ser Phe Gly Ile Val Ser Ala
    130                 135                 140

Arg Gly Ile Lys Thr Val Ala Trp Phe Asn Thr Val Ser Ser Phe Ile
145                 150                 155                 160

Lys Leu Ser Val Leu Cys Leu Ile Ser Leu Thr Val Leu Leu Val Asn
                165                 170                 175

Gly Lys Lys Glu Asn Val Ser Arg Phe Glu Asn Ala Leu Asp Ala Glu
            180                 185                 190

Leu Pro Asn Ala Ser Gln Ile Ala Asp Ala Ile Leu Gln Val Ser Tyr
        195                 200                 205

Ser Tyr Leu Gly Ser Ser Val Leu Ile Val Ile Ala Gly Glu Ile Lys
    210                 215                 220
```

-continued

```
Arg Pro Thr Glu Thr Ile Pro Lys Thr Leu Ile Tyr Gly Ile Ser Ile
225                 230                 235                 240

Val Thr Val Leu Tyr Leu Leu Thr Asn Ile Ser Tyr Leu Ala Val Leu
                245                 250                 255

Thr Ser Gln Glu Ile Ile Phe Ser Asp Ser Val Gly Val Thr Trp Met
            260                 265                 270

Asn Arg Val Phe Pro Ser Ile Gln Trp Ile Ser Ser Phe Leu Ile Ser
        275                 280                 285

Ala Phe Leu Leu Gly Ser Val Ser Cys Gly Ile Val Ser Ala Ser Arg
    290                 295                 300

Val Phe Tyr Ser Ala Ser Gly Glu Gly Glu Phe Pro Ser Ile Tyr Ser
305                 310                 315                 320

Met Leu Asn Asp His His Ser Pro Ala Val Ala Asp Ile Gln Ile Val
                325                 330                 335

Ile Leu Ser Ser Val Ala Ile Ile Ser Ser Ser Ile Ile Tyr Leu Val
                340                 345                 350

Lys Tyr Val Ser Leu Gly Ser Phe Cys Ile Asn Leu Leu Gln Met Ile
            355                 360                 365

Gly Leu Leu Lys Ile Arg Tyr Gln Asn Pro Asp Ile Pro Arg Pro Tyr
        370                 375                 380

Lys Val Trp Leu Pro Phe Ile Phe Gly Ser Ile Ala Leu Ser Leu Phe
385                 390                 395                 400

Leu Ile Phe Thr Pro Val Ile Gln Ser Pro Ser Ile Glu His Val Tyr
                405                 410                 415

Gln Val Val Phe Leu Phe Cys Gly Phe Leu Cys Tyr Trp Leu Gln Ala
                420                 425                 430

Asn Leu Asn Gly His Ala Thr Cys Phe Asp Thr Ile Thr Cys Tyr Cys
            435                 440                 445

Gln Leu Leu Phe Asn Ile Ser Pro Ser Glu Asp Pro Glu Glu Gln Lys
        450                 455                 460

Asn
465

<210> SEQ ID NO 15
<211> LENGTH: 512
<212> TYPE: PRT
<213> ORGANISM: Mus sp.

<400> SEQUENCE: 15

Met Ala Val Ala Gly Ala Lys Arg Arg Ala Val Ala Pro Ala Thr
1               5                   10                  15

Thr Ala Glu Glu Glu Arg Gln Ala Arg Glu Lys Met Leu Glu Ala
            20                  25                  30

Arg Arg Gly Asp Gly Ala Asp Pro Glu Gly Glu Gly Val Thr Leu Gln
        35                  40                  45

Arg Asn Ile Thr Leu Ile Asn Gly Val Ala Ile Ile Val Gly Thr Ile
    50                  55                  60

Ile Gly Ser Gly Ile Phe Val Thr Pro Thr Gly Val Leu Lys Glu Ala
65                  70                  75                  80

Gly Ser Pro Gly Leu Ser Leu Val Val Trp Ala Val Cys Gly Val Phe
                85                  90                  95

Ser Ile Val Gly Ala Leu Cys Tyr Ala Glu Leu Gly Thr Thr Ile Ser
            100                 105                 110

Lys Ser Gly Gly Asp Tyr Ala Tyr Met Leu Glu Val Tyr Gly Ser Leu
```

-continued

```
            115                 120                 125
Pro Ala Phe Leu Lys Leu Trp Ile Glu Leu Leu Ile Ile Arg Pro Ser
    130                 135                 140

Ser Gln Tyr Ile Val Ala Leu Val Phe Ala Thr Tyr Leu Leu Lys Pro
145                 150                 155                 160

Val Phe Pro Thr Cys Pro Val Pro Glu Glu Ala Ala Lys Leu Val Ala
                165                 170                 175

Cys Leu Cys Val Leu Leu Thr Ala Val Asn Cys Tyr Ser Val Lys
                180                 185                 190

Ala Ala Thr Arg Val Gln Asp Ala Phe Ala Ala Lys Leu Leu Ala
                195                 200                 205

Leu Ala Leu Ile Ile Leu Leu Gly Phe Ile Gln Met Gly Lys Asp Ile
    210                 215                 220

Gly Gln Gly Asp Ala Ser Asn Leu His Gln Lys Leu Ser Phe Glu Gly
225                 230                 235                 240

Thr Asn Leu Asp Val Gly Asn Ile Val Leu Ala Leu Tyr Ser Gly Leu
                245                 250                 255

Phe Ala Tyr Gly Gly Trp Asn Tyr Leu Asn Phe Val Thr Glu Glu Met
                260                 265                 270

Ile Asn Pro Tyr Arg Asn Leu Pro Leu Ala Ile Ile Ser Leu Pro
                275                 280                 285

Ile Val Thr Leu Val Tyr Val Leu Thr Asn Leu Ala Tyr Phe Thr Thr
    290                 295                 300

Leu Ser Thr Asn Gln Met Leu Thr Ser Glu Ala Val Ala Val Asp Phe
305                 310                 315                 320

Gly Asn Tyr His Leu Gly Val Met Ser Trp Ile Ile Pro Val Phe Val
                325                 330                 335

Gly Leu Ser Cys Phe Gly Ser Val Asn Gly Ser Leu Phe Thr Ser Ser
                340                 345                 350

Arg Leu Phe Phe Val Gly Ser Arg Glu Gly His Leu Pro Ser Ile Leu
                355                 360                 365

Ser Met Ile His Pro Gln Leu Leu Thr Pro Val Pro Ser Leu Val Phe
    370                 375                 380

Thr Cys Val Met Thr Leu Met Tyr Ala Phe Ser Arg Asp Ile Phe Ser
385                 390                 395                 400

Ile Ile Asn Phe Phe Ser Phe Asn Trp Leu Cys Val Ala Leu Ala
                405                 410                 415

Ile Ile Gly Met Met Trp Leu Arg Phe Lys Lys Pro Glu Leu Glu Arg
                420                 425                 430

Pro Ile Lys Val Asn Leu Ala Leu Pro Val Phe Phe Ile Leu Ala Cys
                435                 440                 445

Leu Phe Leu Ile Ala Val Ser Phe Trp Lys Thr Pro Leu Glu Cys Gly
    450                 455                 460

Ile Gly Phe Ala Ile Ile Leu Ser Gly Leu Pro Val Tyr Phe Phe Gly
465                 470                 475                 480

Val Trp Trp Lys Asn Lys Pro Lys Trp Ile Leu Gln Val Ile Phe Ser
                485                 490                 495

Val Thr Val Leu Cys Gln Lys Leu Met Gln Val Val Pro Gln Glu Thr
                500                 505                 510
```

<210> SEQ ID NO 16
<211> LENGTH: 512
<212> TYPE: PRT
<213> ORGANISM: Rattus sp.

<400> SEQUENCE: 16

Met Val Ala Ser Thr Lys Tyr Glu Val Ala Ala Gln Asn Glu Ala Asp
1               5                   10                  15

Glu Ala Asp Gly Ser Ala Gln Gly Asp Gly Ala Gly Pro Ala Ala Glu
            20                  25                  30

Gln Val Lys Leu Lys Lys Glu Ile Ser Leu Leu Asn Gly Val Cys Leu
        35                  40                  45

Ile Val Gly Asn Met Ile Gly Ser Gly Ile Phe Val Ser Pro Lys Gly
    50                  55                  60

Val Leu Met Tyr Ser Ala Ser Phe Gly Leu Ser Leu Val Ile Trp Ala
65              70                  75                  80

Val Gly Gly Ile Phe Ser Val Phe Gly Ala Leu Cys Tyr Ala Glu Leu
            85                  90                  95

Gly Thr Thr Ile Lys Lys Ser Gly Ala Ser Tyr Ala Tyr Ile Leu Glu
        100                 105                 110

Ala Phe Gly Gly Phe Leu Ala Phe Ile Arg Leu Trp Thr Ser Leu Leu
    115                 120                 125

Ile Ile Glu Pro Thr Ser Gln Ala Val Ile Ala Ile Thr Phe Ala Asn
130                 135                 140

Tyr Met Val Gln Pro Leu Phe Pro Ser Cys Gly Ala Pro Tyr Ala Ala
145                 150                 155                 160

Gly Arg Leu Leu Ala Ala Ala Cys Ile Cys Leu Leu Thr Phe Ile Asn
            165                 170                 175

Cys Ala Tyr Val Lys Trp Gly Thr Leu Val Gln Asp Ile Phe Thr Tyr
        180                 185                 190

Ala Lys Val Leu Ala Leu Ile Ala Val Ile Ile Ala Gly Ile Val Arg
    195                 200                 205

Leu Gly Gln Gly Ala Thr Thr Asn Phe Glu Asp Ser Phe Glu Gly Ser
210                 215                 220

Ser Phe Ala Met Gly Asp Ile Ala Leu Ala Leu Tyr Ser Ala Leu Phe
225                 230                 235                 240

Ser Tyr Ser Gly Trp Asp Thr Leu Asn Tyr Val Thr Glu Glu Ile Arg
            245                 250                 255

Asn Pro Glu Arg Asn Leu Pro Leu Ser Ile Gly Ile Ser Met Pro Ile
        260                 265                 270

Val Thr Ile Ile Tyr Leu Leu Thr Asn Val Ala Tyr Tyr Ser Val Leu
    275                 280                 285

Asp Ile Lys Asp Ile Leu Ala Ser Asp Ala Val Ala Val Thr Phe Ala
290                 295                 300

Asp Gln Ile Phe Gly Ile Phe Asn Trp Thr Ile Pro Leu Ala Val Ala
305                 310                 315                 320

Leu Ser Cys Phe Gly Gly Leu Asn Ala Ser Ile Val Ala Ala Ser Arg
            325                 330                 335

Leu Leu Phe Val Gly Ser Arg Glu Gly His Leu Pro Asp Ala Ile Cys
        340                 345                 350

Met Ile His Val Glu Arg Phe Thr Pro Val Pro Ser Leu Leu Phe Asn
    355                 360                 365

Gly Ile Leu Ala Leu Val Tyr Leu Cys Val Glu Asp Ile Phe Gln Leu
370                 375                 380

Ile Asn Tyr Tyr Ser Phe Ser Tyr Trp Phe Phe Val Gly Leu Ser Ile
385                 390                 395                 400

Val Gly Gln Leu Tyr Leu Arg Trp Lys Glu Pro Asp Arg Pro Arg Pro

```
                    405                 410                 415
Leu Lys Leu Ser Leu Phe Phe Pro Ile Val Phe Cys Leu Cys Thr Ile
                420                 425                 430

Phe Leu Val Ala Val Pro Leu Tyr Ser Asp Thr Ile Asn Ser Leu Ile
                435                 440                 445

Gly Ile Gly Ile Ala Leu Ser Gly Leu Pro Phe Tyr Phe Leu Ile Ile
                450                 455                 460

Arg Val Pro Glu His Lys Arg Pro Leu Cys Leu Arg Arg Ile Val Ala
465                 470                 475                 480

Ser Thr Thr Arg Tyr Leu Gln Ile Ile Cys Met Ser Val Ala Ala Glu
                485                 490                 495

Met Asp Leu Glu Asp Gly Glu Leu Pro Lys Gln Gly Pro Lys Ser Lys
                500                 505                 510

<210> SEQ ID NO 17
<211> LENGTH: 502
<212> TYPE: PRT
<213> ORGANISM: Rattus sp.

<400> SEQUENCE: 17

Met Val Arg Lys Pro Val Val Ala Thr Ile Ser Lys Gly Gly Tyr Leu
1               5                   10                  15

Gln Gly Asn Met Ser Gly Arg Leu Pro Ser Met Gly Asp Gln Glu Pro
                20                  25                  30

Pro Gly Gln Glu Lys Val Val Leu Lys Lys Lys Ile Thr Leu Leu Arg
            35                  40                  45

Gly Val Ser Ile Ile Ile Gly Thr Val Ile Gly Ser Gly Ile Phe Ile
        50                  55                  60

Ser Pro Lys Gly Ile Leu Gln Asn Thr Gly Ser Val Gly Met Ser Leu
65                  70                  75                  80

Val Phe Trp Ser Ala Cys Gly Val Leu Ser Leu Phe Gly Ala Leu Ser
                85                  90                  95

Tyr Ala Glu Leu Gly Thr Ser Ile Lys Lys Ser Gly Gly His Tyr Thr
                100                 105                 110

Tyr Ile Leu Glu Val Phe Gly Pro Leu Leu Ala Phe Val Arg Val Trp
            115                 120                 125

Val Glu Leu Leu Val Ile Arg Pro Gly Ala Thr Ala Val Ile Ser Leu
        130                 135                 140

Ala Phe Gly Arg Tyr Ile Leu Glu Pro Phe Phe Ile Gln Cys Glu Ile
145                 150                 155                 160

Pro Glu Leu Ala Ile Lys Leu Val Thr Ala Val Gly Ile Thr Val Val
                165                 170                 175

Met Val Leu Asn Ser Thr Ser Val Ser Trp Ser Ala Arg Ile Gln Ile
                180                 185                 190

Phe Leu Ile Phe Cys Lys Leu Thr Ala Ile Leu Ile Ile Ile Val Pro
            195                 200                 205

Gly Val Ile Gln Leu Ile Lys Gly Gln Thr His His Phe Lys Asp Ala
        210                 215                 220

Phe Ser Gly Arg Asp Thr Ser Leu Met Gly Leu Pro Leu Ala Phe Tyr
225                 230                 235                 240

Tyr Gly Met Tyr Ala Tyr Ala Gly Trp Phe Tyr Leu Asn Phe Ile Thr
                245                 250                 255

Glu Glu Val Asp Asn Pro Glu Lys Thr Ile Pro Leu Ala Ile Cys Ile
                260                 265                 270
```

Ser Met Ala Ile Ile Thr Val Gly Tyr Val Leu Thr Asn Val Ala Tyr
            275                 280                 285

Phe Ile Thr Ile Ser Ala Glu Glu Leu Leu Gln Ser Ser Ala Val Ala
            290                 295                 300

Val Ile Phe Ser Glu Arg Leu Leu Gly Lys Phe Ser Leu Ala Val Pro
305                 310                 315                 320

Ile Phe Val Ala Leu Ser Cys Phe Gly Ser Met Asn Gly Gly Val Phe
            325                 330                 335

Ala Val Ser Arg Leu Phe Tyr Val Ala Ser Arg Glu Gly His Leu Pro
            340                 345                 350

Glu Ile Leu Ser Met Ile His Val His Lys His Thr Pro Leu Pro Ala
            355                 360                 365

Val Ile Val Leu His Pro Leu Thr Met Val Met Leu Phe Ser Gly Asp
            370                 375                 380

Leu Tyr Ser Leu Leu Asn Phe Leu Ser Phe Ala Arg Trp Leu Phe Met
385                 390                 395                 400

Gly Leu Ala Val Ala Gly Leu Ile Tyr Leu Arg Tyr Lys Arg Pro Asp
            405                 410                 415

Met His Arg Pro Phe Lys Val Pro Leu Phe Ile Pro Ala Leu Phe Ser
            420                 425                 430

Phe Thr Cys Leu Phe Met Val Val Leu Ser Leu Tyr Ser Asp Pro Phe
            435                 440                 445

Ser Thr Gly Val Gly Phe Leu Ile Thr Leu Thr Gly Val Pro Ala Tyr
            450                 455                 460

Tyr Leu Phe Ile Val Trp Asp Lys Lys Pro Lys Trp Phe Arg Arg Leu
465                 470                 475                 480

Ser Asp Arg Ile Thr Arg Thr Leu Gln Ile Ile Leu Glu Val Val Pro
            485                 490                 495

Glu Asp Ser Lys Glu Leu
            500

<210> SEQ ID NO 18
<211> LENGTH: 487
<212> TYPE: PRT
<213> ORGANISM: Rattus sp.

<400> SEQUENCE: 18

Met Glu Glu Thr Ser Pro Arg Arg Arg Glu Asp Glu Lys Ser Val
1               5                   10                  15

His Ser Thr Glu Pro Lys Thr Thr Ser Leu Gln Lys Glu Val Gly Leu
            20                  25                  30

Leu Ser Gly Ile Cys Ile Ile Val Gly Thr Ile Ile Gly Ser Gly Ile
            35                  40                  45

Phe Ile Ser Pro Lys Ser Val Leu Ala Asn Thr Glu Ser Val Gly Pro
            50                  55                  60

Cys Leu Ile Ile Trp Ala Ala Cys Gly Val Leu Ala Thr Leu Gly Ala
65                  70                  75                  80

Leu Cys Phe Ala Glu Leu Gly Thr Met Ile Thr Lys Ser Gly Gly Glu
            85                  90                  95

Tyr Pro Tyr Leu Met Glu Ala Phe Gly Pro Ile Pro Ala Tyr Leu Phe
            100                 105                 110

Ser Trp Thr Ser Leu Ile Val Met Lys Pro Ser Ser Phe Ala Ile Ile
            115                 120                 125

Cys Leu Ser Phe Ser Glu Tyr Tyr Cys Ala Ala Phe Tyr Leu Gly Cys
            130                 135                 140

Arg Pro Pro Ala Val Val Lys Leu Leu Ala Ala Ala Ile Leu
145                 150                 155                 160

Leu Ile Thr Thr Val Asn Ala Leu Ser Val Arg Leu Gly Ser Tyr Val
            165                 170                 175

Gln Asn Val Phe Thr Ala Ala Lys Leu Val Ile Val Ala Ile Ile Ile
            180                 185                 190

Ile Ser Gly Leu Val Leu Leu Ala Gln Gly Asn Val Lys Asn Phe Gln
            195                 200                 205

Asn Ser Phe Glu Gly Ser Gln Thr Ser Val Gly Ser Ile Ser Leu Ala
210                 215                 220

Phe Tyr Asn Gly Leu Trp Ala Tyr Asp Gly Trp Asn Gln Leu Asn Tyr
225                 230                 235                 240

Ile Thr Glu Glu Leu Arg Asn Pro Tyr Arg Asn Leu Pro Met Ala Ile
            245                 250                 255

Val Ile Gly Ile Pro Leu Val Thr Val Cys Tyr Ile Leu Met Asn Ile
            260                 265                 270

Ala Tyr Phe Thr Val Met Thr Pro Thr Glu Leu Leu Gln Ser Gln Ala
            275                 280                 285

Val Ala Val Thr Phe Gly Asp Arg Val Leu Tyr Pro Ala Ser Trp Val
290                 295                 300

Val Pro Leu Phe Val Ala Phe Ser Thr Ile Gly Ala Ala Asn Gly Thr
305                 310                 315                 320

Cys Phe Thr Ala Gly Arg Leu Ile Tyr Val Ala Gly Arg Glu Gly His
            325                 330                 335

Met Leu Lys Val Leu Ser Tyr Ile Ser Val Lys Arg Leu Thr Pro Ala
            340                 345                 350

Pro Ala Leu Val Phe Tyr Gly Ile Ala Ile Ile Tyr Ile Ile Pro
            355                 360                 365

Gly Asp Ile Asn Ser Leu Val Asn Tyr Phe Ser Phe Ala Ala Trp Leu
370                 375                 380

Phe Tyr Gly Met Thr Ile Leu Gly Leu Val Val Met Arg Phe Thr Arg
385                 390                 395                 400

Lys Asp Leu Glu Arg Pro Ile Lys Val Pro Ile Phe Ile Pro Ile Ile
            405                 410                 415

Val Ile Leu Val Ser Val Phe Leu Ile Leu Ala Pro Ile Ile Ser Ser
            420                 425                 430

Pro Ala Trp Glu Tyr Leu Tyr Cys Val Leu Phe Ile Leu Ser Gly Leu
            435                 440                 445

Ile Phe Tyr Phe Leu Phe Val His Tyr Lys Phe Arg Trp Ala Gln Lys
            450                 455                 460

Ile Ser Arg Pro Ile Thr Lys His Leu Gln Met Leu Met Glu Val Val
465                 470                 475                 480

Pro Pro Glu Lys Asp Pro Glu
            485

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: CDS
<222> LOCATION: (1)..(27)

```
<400> SEQUENCE: 19 gaa gaa agt gcg gcc gca agc cag gac                              27
Glu Glu Ser Ala Ala Ala Ser Gln Asp
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 20

Glu Glu Ser Ala Ala Ala Ser Gln Asp
 1               5

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: CDS
<222> LOCATION: (1)..(27)

<400> SEQUENCE: 21 gaa gaa agt gcg gcc gca gat gag gac                              27
Glu Glu Ser Ala Ala Ala Asp Glu Asp
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 22

Glu Glu Ser Ala Ala Ala Asp Glu Asp
 1               5
```

SODIUM-INDEPENDENT TRANSPORTER CARRYING ACIDIC AMINO ACID AND ITS GENE

The present application is a Continuation of PCT Application No. PCT/JP03/01614, filed on Feb. 17, 2003, which in turn claimed the prior benefit of Japanese Application 2002-040608, filed on Feb. 18, 2002.

TECHNICAL FIELD

The present invention relates to a protein associated with the sodium-independent transport of acidic amino acids and its analogue, fusion protein thereof, as well as a gene encoding said protein. The present invention also relates to a method for controlling the cell proliferation or for altering the in vivo pharmacokinetics of a pharmaceutical, toxic substance or xenobiotics by modulating an ability to transport acidic amino acids and its analogue possessed by a protein associated with the sodium-independent transport of acidic amino acids and its analogue, by means of employing said protein, its fusion protein, its specific antibody, or its function-promoting substance or function-suppressing substance, as well as an agent for controlling an ability to transport acidic amino acids and its analogue comprising said substances.

BACKGROUND ART

A cell always requires the uptake of an amino acid as a nutrition, and such a function is exerted by an amino acid transporter which is a membrane protein existing in a cell membrane. The amino acid transporter is distributed in a specific site in each tissue in a multicellular organism and plays an important role in expressing the specific function of each tissue. For example, in kidney cells and small intestine, it plays a role for epithelial absorption of amino acid in lumen and, in nerve tissues, it is in charge of recovery of amino acid as a neurotransmitter released as a result of neurotransmission and also of supply of amino acid as a precursor for neurotransmitter to nerve cells. Further, it exists in blood-brain barrier and placental barrier and makes permeation of the amino acid possible.

With regard to an amino acid transport mechanism, its identification and classification have been conducted using cultured cells and membrane specimens since 1960's and, reflecting the multiplicity of amino acid molecules, many transport systems have been described. However, there has been no independent transport system for each amino acid but most of the amino acid transports have been conducted by a few kinds of transport systems which transport several amino acids having similar side chains (Christensen, *Physiol. Rev.*, volume 70, page 43, 1990).

Transport of acidic amino acids such as glutamic acid and aspartic acid having carboxyl group on a side chain has been believed to be carried out by both of a sodium-dependent transporter which requires sodium ion for its function and a sodium-independent transporter which does not require sodium ion for its function.

However, in a conventional method, it is difficult to analyze the details of the transport of an amino acid or its analogue via the acidic amino acid transport system and the in vivo functional roles, and it has been desired to enable a detailed functional analysis by isolating a gene of acidic amino acid transporter responsible for the function of the acidic amino acid transport system.

With regard to sodium-dependent acidic amino acid transporters, five kinds of glutamate transporters—EAAC1, GLT-1, GLAST, EAAT4 and EAAT5—have been cloned (Kanai, *Curr. Opin. Cell Biol.*, volume 9, page 565, 1997; Kanai and Endou, *Curr. Drug Metab.*, volume 2, page 339, 2001).

With regard to sodium-independent transporters, LAT1 (Kanai, et al., *J. Biol. Chem.*, volume 273, pages 23629-23632, 1998) and LAT 2 (Segawa, et al., *J. Biol. Chem.*, volume 274, pages 19745-19751, 1999) have been cloned as neutral amino acid transporters corresponding to a transport system L. It was also shown that LAT1 and LAT2 function only when they coexist with a cofactor 4F2hc which is a single membrane-spanning type protein. LAT1 shows an exchange transport activity which transports large-sized neutral amino acids such as leucine, isoleucine, valine, phenylalanine, tyrosine, tryptophan, methionine and histidine while LAT2 shows a broad substrate selectivity transporting small-sized neutral amino acids such as glycine, alanine, serine, cysteine and threonine in addition to large-sized neutral amino acids and they are not acidic amino transporters.

With regard to proteins analogous to LAT1 and LAT2, the above-mentioned $y^+$LAT1 and $y^+$LAT2 having the functions of a transport system $y^+$L which transports neutral amino acids and basic amino acids have been cloned (Torrents, et al., *J. Biol. Chem.*, volume 273, pages 32437-32445, 1998). It was also revealed that both of $y^+$LAT1 and $y^+$LAT2 function only when being coexisting with a cofactor 4F2hc. $y^+$LAT1 and $y^+$LAT2 mainly transport glutamine, leucine and isoleucine as neutral amino acids and do not transport acidic amino acids.

With regard to a transporter which requires a cofactor 4F2hc for expressing its function, Asc-1 which is a protein analogous to LAT1 to LAT2 was cloned (Fukasawa, et al., *J. Biol. Chem.*, 275: 9690-9698, 2000). Asc-1 selectively transports alanine, serine, cysteine, threonine, glycine, etc., shows a substrate selectivity of amino acid transport system asc and does not transport acidic amino acids.

With regard to a transporter which requires another cofactor rBAT having an analogous structure to 4F2hc for expressing its function, BAT1 which is a protein analogous to LAT1 and LAT2 was cloned (Chairoungdua, et al., *J. Biol. Chem.*, 274: 28845-28848, 1999). BAT1 transports cystine, neutral amino acids and basic amino acids and does not transport acidic amino acids.

As described above, molecular entity of a transporter which functions by binding to 4F2hc and rBAT was characterized and, the presence of a group of transporters which achieves a transport ability by forming heterodimer with a single membrane-spanning type protein and a heterodimeric amino acid transporter family was established.

Further, with regard to a transporter requiring a cofactor 4F2hc for expressing its function, xCT which is a protein analogous to LAT1 and LAT2 was cloned (Sato, et al., *J. Biol. Chem.*, 274; 11455-11458, 1999). xCT transports cystine, glutamic acid and sodium aminoadipate in a sodium-independent manner and corresponds to an amino acid transport system Xc. xCT needs a negative charge of side chain of amino acid for recognition of substrate and is classified under sodium-independent acidic amino acid transporters (Kanai and Endou, *Curr. Drug Metab.*, volume 2, page 339, 2001).

xCT transports glutamic acid but does not transport aspartic acid and its transport is suppressed by cystine. In addition, xCT is a transporter where expression is induced by oxidative stress and, except a few cases, its expression in common normal tissues is not detected. However, it has been reported that there is a sodium-independent glutamic acid and aspartic acid transporter which is not suppressed by cystine (Christensen, *Physiol. Rev.*, volume 70, page 43, 1990) and it has been suggested that there is a sodium-independent acidic amino acid transporter other than xCT which has not been identified.

Further, Asc-2 which is a protein having an analogous structure to LAT1 and LAT2 and binds to unidentified protein other than rBAT or 4F2hc was cloned (Chairoungdua, et al., *J. Biol. Chem.*, 276: 49390-49399, 2001). Asc-2 is not expressed in a cell membrane by itself, however, by preparing a fusion protein with 4F2hc or rBAT, it transfers to a cell membrane as a fusion protein and a transport activity can be detected. When Asc-2 is expressed in a cell membrane as a fusion protein with 4F2hc or rBAT, it shows a characteristic of a sodium-independent neutral amino acid transport system asc.

DISCLOSURE OF THE INVENTION

An object of the present invention is to provide a gene of a transporter which transports acidic amino acids such as glutamic acid and aspartic acid in a sodium-independent manner and also to provide a sodium-independent acidic amino acid transporter which is a polypeptide encoded by the gene.

Other objects will be apparent from the following description.

The present inventors have searched the EST (expressed sequence tag) database using a base sequence of translation region of cDNA of BAT1 and identified a base sequence analogous to BAT1. A base sequence of cDNA clone corresponding to the sequence has been decided and clarified that it encodes a novel protein. Further, a fusion protein of the translated product of the gene with 4F2hc or rBAT has been prepared and expressed in a cell membrane of oocyte of Xenopus. As a result, it has been clarified that the function of the translated product of the gene is a sodium-independent transporter which transports acidic amino acids such as glutamic acid and aspartic acid whereby the present invention has been achieved.

Thus, the present invention relates to a protein selected from the following (A) or (B).

(A) protein comprising an amino acid sequence represented by SEQ ID NO: 1.

(B) protein comprising an amino acid sequence where one or several amino acid(s) is/are deleted, substituted or added in the amino acid sequence represented by SEQ ID NO: 1 and having an ability of transport of acidic amino acids or its analogue in a sodium-independent manner.

The present invention also relates to a gene comprising DNA selected from the following (a) and (b).

(a) DNA comprising a base sequence represented by SEQ ID NO: 2.

(b) DNA hybridizing with DNA comprising the base sequence represented by SEQ ID NO: 2 under a stringent condition and encodes a protein having an ability of transport of acidic amino acids or its analogue in a sodium-independent manner.

The novel protein of the present invention having an ability of transport of acidic amino acids and its analogue in a sodium-independent manner or, in other words, an amino acid transporter AGT1 (aspartate/glutamate transporter 1) is expressed in a cell membrane and has an ability of transport (uptake) of acidic amino acids such as glutamic acid and aspartic acid in a highly affinitive manner by preparing a fusion protein with 4F2hc or rBAT.

Incidentally, the sodium-independent transporter AGT1 of the present invention which transports acidic amino acids is mainly expressed in the kidney in vivo.

BRIEF DESCRIPTION OF THE DRAWINGS

FIG. 1 shows the amino acid sequences of mouse AGT1 (SEQ ID NO: 1), mouse Asc-2 (SEQ ID NO: 14), rat LAT1 (SEQ ID NO: 15), rat y$^+$LAT1 (SEQ ID NO: 16), mouse xCT (SEQ ID NO: 17) and rat BAT1 (SEQ ID NO: 18) for comparison with each other. The assumed membrane-spanning sites are shown by lines. A conserved cystine residue is shown by *, assumed cAMP-dependent phosphorylation site is shown by #, an assumed C-kinase-dependant phosphorylation site is shown by + and an assumed tyrosine phosphorylation site is shown by &.

PDC: L-trans-pyrrolidine-2,4-dicarboxylate; DHK: dihydrokainate; **: the case where p<0.01 in Student's t-test to the data which does not constitute a pair.

Figure 13:
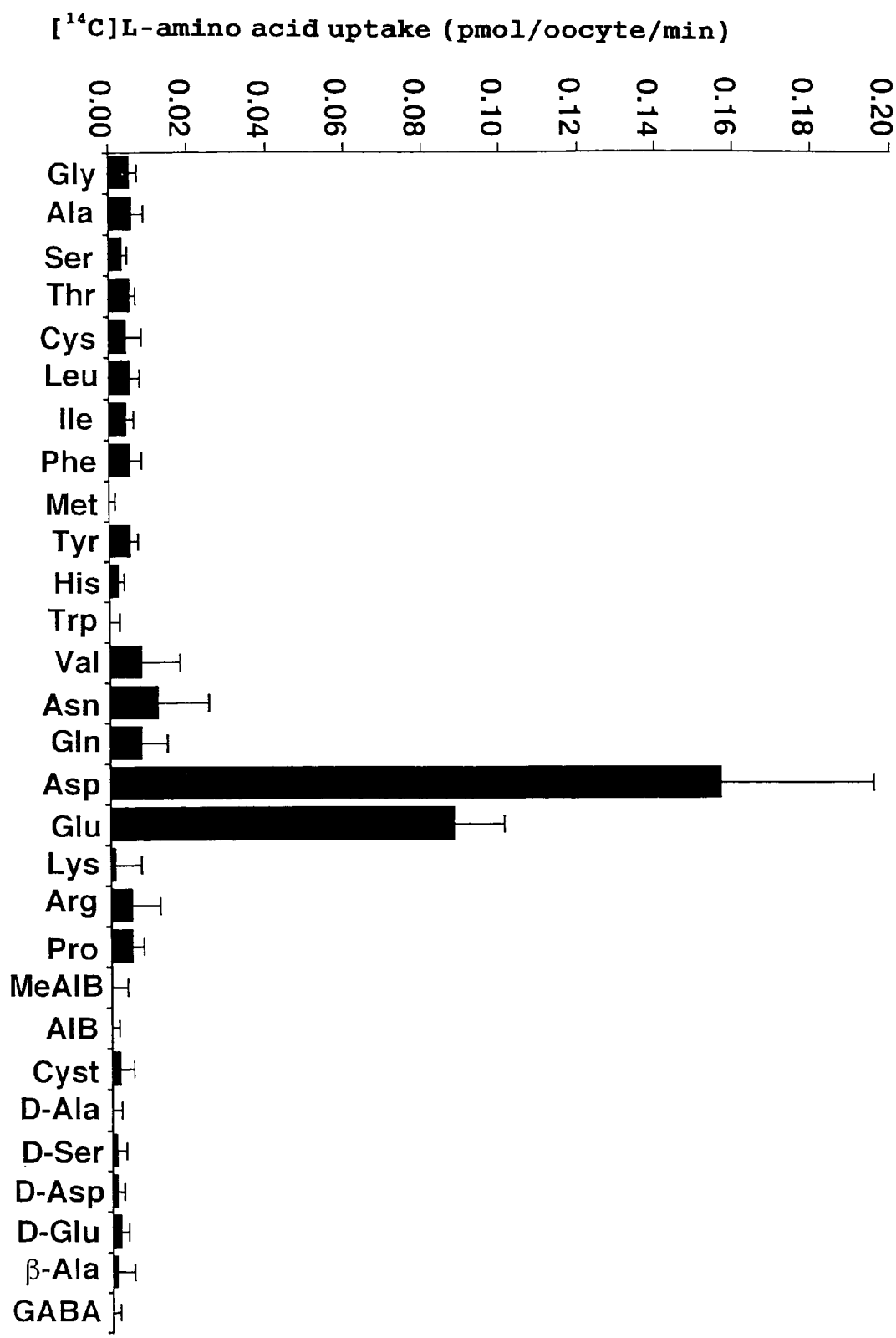

FIG. 13 shows the result of investigating the uptake of radio-labeled amino acid by an oocyte into which a fusion protein (AGT1-4F2hc) gene cRNA of AGT1 with 4F2hc was injected.

BEST MODE FOR CARRYING OUT THE INVENTION

SEQ ID NO: 1 in the Sequence Listing which will be shown later represents an amino acid sequence (478 amino acids) of a sodium-independent transporter (mouse AGT1) derived from mouse transporting acidic amino acids and SEQ ID NO: 2 represents an amino acid sequence (478 amino acids) of protein encoded in a full-length cDNA base sequence (about 2.1 kbp) of the gene and a translation region thereof.

When the amino acid sequence represented by SEQ ID NO: 1 or the base sequence represented by SEQ ID NO: 2 which will be mentioned later was subjected to a homology search for all sequences included in the known protein databases (NBRF and SWISS-PROT) and DNA databases (GenBank and EMBL), no sequence was identical, whereby the sequence is believed to be novel.

With regard to the protein of the present invention, there may be exemplified, in addition to the one having an amino acid sequence represented by SEQ ID NO: 1, a protein having the amino acid sequence where one or several amino acid(s) is/are deleted, substituted or added in the amino acid sequence represented by SEQ ID NO: 1. Deletion, substitution or addition of amino acid(s) may be within such an extent that transport activity of a neutral amino acid is not lost and, usually, it is from 1 to about 96 or, preferably, from 1 to about 48. Such a protein usually has a homology to the amino acid sequence represented by SEQ ID NO: 1 to an extent of 1 to 80%, preferably, 1 to 90%.

With regard to the gene of the present invention, in addition to the one having a base sequence represented by SEQ ID NO: 2, it includes a gene containing DNA which can be hybridized with DNA having a base sequence represented by SEQ ID NO: 2 under a stringent condition. With regard to the DNA which can be hybridized, any substance will do so far as the protein encoded by the DNA has an ability of transporting a neutral amino acid. Such a DNA usually has a homology of base sequence of more than 70%, preferably more than 80% with the base sequence represented by SEQ ID NO: 2. Such a DNA includes a variant gene found in nature, an artificially modified variant gene, a homologous gene derived from other organism, and the like.

In the present invention, a hybridization under a stringent condition is usually carried out in such a manner that a hybridization is carried out for about 12 hours under the temperature of 37 to 42° C. in a hybridization solution of 5×SSC or having the identical salt concentration therewith, a preliminary washing is carried out upon necessity using a solution of 5×SSC or having the identical salt concentration therewith and then washing is carried out in a solution of 1×SSC or having the identical salt concentration therewith.

The sodium-independent transporter gene which transports acidic amino acids according to the present invention can be isolated and obtained by carrying out a screening using a tissue or a cell of appropriate mammals as a gene source. Examples of the mammals are non-human animals such as dog, cattle, horse, goat, sheep, monkey, pig, rabbit, rat and mouse, and in addition to those, human beings.

Screening and isolation of gene is able to be advantageously carried out by, for example, a homology cloning method.

For example, mouse or human kidney is used as a gene source and mRNA (poly(A)$^+$RNA) is prepared therefrom. Then a cDNA library is constructed therefrom and cDNA is screened using a probe corresponding to a sequence analogous to BAT1 (such as GenBank™/EBI/DDBJ accession No AI314100) obtained by searching the EST (expressed sequence tag) database whereby a clone containing cDNA of Asc-2 gene can be obtained.

With regard to the obtained cDNA, the base sequence is determined by a conventional method and translation region is analyzed, whereby an amino acid sequence of the protein encoded thereby, i.e. AGT1, can be determined.

The fact that the resulting cDNA is a sodium-independent transporter which transports acidic amino acids, in other words, the gene product encoded with cDNA is a sodium-independent transporter which transports acidic amino acids can be tested, for example, by the following method. Thus, cDNA encoding a fusion protein of AGT1 with 4F2hc or rBAT is prepared using the resulting cDNA of AGT1 gene, then RNA (cRNA) which is prepared from the cDNA and complementary thereto is introduced into the oocyte to be expressed and an ability of transport (uptake) of acidic amino acids into the cells can be confirmed by measuring the uptake of the substrate into cells by a common uptake test using an appropriate acidic amino acid as a substrate (Kanai and Hediger, *Nature*, volume 360, pages 467-471, 1992).

AGT1 protein is synthesized by an in vitro translation method (Hediger, et al., *Biochim. Biophys. Acta*, volume 1064, page 360, 1991) using RNA (cRNA) prepared from the resulting cDNA of AGT1 gene and being complementary thereto and the size of the protein or the presence of sugar, etc. can be investigated by means of electrophoresis.

Since cDNA of 4F2hc gene has been reported already (Fukasawa, et al., *J. Biol. Chem.*, 275: 9690-9698, 2000), it is possible to easily prepare a gene of 4F2hc from the sequence information by a PCR or the like.

Since cDNA of rBAT gene has been also reported already (Segawa, H., et al., *Biochem. J*, 328: 657-664, 2000), it is possible to easily prepare a gene of rBAT from the sequence information by a PCR or the like.

cDNA encoding a fusion protein of AGT1 with 4F2hc or rBAT is easily prepared by a PCR or the like from cDNA of AGT1 gene, cDNA of 4F2hc gene or cDNA of rBAT gene.

The characteristic of AGT1 such as substrate selectivity of AGT1 can be investigated by applying the similar uptake experiment to the expressed cells.

Homologous gene, chromosome gene, etc. derived from different tissues and different organisms can be isolated by screening an appropriate cDNA library or genomic DNA library prepared from different gene sources using the resulting cDNA of AGT1 gene.

It is also possible to isolate a gene from a cDNA library or a genomic DNA library by a conventional PCR (polymerase chain reaction) method using a synthetic primer designed on the basis of information of the disclosed base sequence of the gene of the present invention (the base sequence represented by SEQ ID NO: 2 or a part thereof).

DNA library such as a cDNA library or a genomic DNA library may be prepared by a method mentioned, for example, in "Molecular Cloning" by Sambrook, J., Fritsh, E. F. and Manitis, T. (Cold Spring Harbor Press, 1989). When there is a commercially available library, it can be used as well.

The sodium-independent transporter which transports acidic amino acids according to the present invention and the gene (AGT1) thereof may be produced by, for example, a gene recombination technique using cDNA encoding therefor. For example, DNA (such as cDNA) encoding AGT1 is incorporated into an appropriate expression vector and the resulting recombinant DNA can be introduced into an appropriate host cell. With regard to an expression system (host-vector system) for the production of polypeptide, there may be exemplified expression systems of bacteria, yeasts, insect cells and mammalian cells. Among those, it is preferred to use insect cells and mammalian cells for the preparation of functional proteins.

A fusion protein of the sodium-independent transporter which transports acidic amino acids according to the present invention with 4F2hc or rBAT or a gene thereof (AGT 1-4F2hc or AGT 1-rBAT) may be produced, for example, by a gene recombination technique using cDNA encoding it. For example, DNA (such as cDNA) encoding AGT1-4F2hc or AGT1-rBAT is incorporated into an appropriate expression vector and the resulting recombinant DNA can be introduced into an appropriate host cell. With regard to an expression system (host-vector system) for the production of polypeptide, there may be exemplified expression systems of bacteria, yeasts, insect cells and mammalian cells. Among those, it is preferred to use insect cells and mammalian cells for the preparation of functional proteins.

For example, when polypeptide is expressed in mammalian cells, DNA encoding the sodium-independent transporter AGT1 which transports acidic amino acids according to the present invention or DNA encoding a fusion protein of AGT1 with 4F2hc or rBAT is inserted into a downstream side of an appropriate promoter (such as cytomegalovirus promoter, SV40 promoter, LTR promoter, elongation 1$a$ promoter, etc.) in an appropriate expression vector (such as adenovirus vector, retrovirus vector, papilloma virus vector, vaccinia virus vector, SV40 vector, etc.) so that expression vector is constructed. Then, an appropriate animal cell is transformed using the resulting expression vector and the transformant is incubated in an appropriate medium whereby a desired polypeptide is produced. Examples of the mammalian cell used as a host are cell strains such as simian COS-7 cell, Chinese hamster CHO cell and human HeLa cell.

Accordingly, the present invention provides a vector, preferably an expression vector, which contains a gene encoding the above-mentioned gene of the present invention or for a protein in the gene and also provides a host cell (transformant) which is transformed using the vector.

With regard to the DNA encoding the sodium-independent transporter AGT1 which transports acidic amino acids, cDNA having the base sequence represented by SEQ ID NO: 2 may be used, for example, in addition to that, DNA corresponding to the amino acid sequence is designed and may be used as DNA encoding polypeptide without limiting to the above-mentioned cDNA sequence. In that case, with regard to a codon encoding one amino acid, 1 to 6 kinds are known for each, and although the used codon may be optionally selected, frequency of use of a codon of a host utilized for the expression may be taken into consideration to design a sequence having higher expression efficiency. DNA having the designed base sequence can be prepared by chemical synthesis of DNA, binding to fragmentation of the above-mentioned cDNA, partial modification of the base sequence, and the like. The artificial partial modification of and introduction of variation into base sequence may be carried out utilizing a primer comprising synthetic oligonucleotide encoding the desired modification by a site-specific mutagenesis (Mark, D. F., et al., *Proceedings of National Academy of Sciences*, volume 81, page 5662 (1984), etc.).

DNA encoding a fusion protein (AGT1-4F2hc or AGT1-rBAT) of the sodium-independent transporter AGT1 which transports acidic amino acids with 4F2hc or rBAT may be prepared, for example, using a base sequence represented by SEQ ID NO: 2 or SEQ ID NO: 4 or using cDNA having a base sequence represented by SEQ ID NO: 6 and, moreover, DNA corresponding to the amino acid sequence is designed and can be used as DNA encoding polypeptide without limiting to the above-mentioned cDNA sequences. In that case, with regard to a codon encoding one amino acid, 1 to 6 kinds are known for each, and although the used codon may be optionally selected, frequency of use of a codon of a host utilized for the expression may be taken into consideration to design a sequence having higher expression efficiency may be designed. DNA having the designed base sequence can be prepared by chemical synthesis of DNA, binding to fragmentation of the above-mentioned cDNA, partial modification of the base sequence, and the like. The artificial partial modification and introduction of variation into base sequence may be carried out utilizing a primer comprising synthetic oligo-nucleotide encoding the desired modification by a site-specific mutagenesis (Mark, D. F., et al., *Proceedings of National Academy of Sciences*, volume 81, page 5662 (1984), etc.).

The present invention also provides a nucleotide containing a partial sequence of continuous 14 or more bases, preferably 20 or more bases, in the base sequence represented by SEQ ID NO: 2 or the complementary sequence thereof.

The nucleotide of the present invention can be used as a probe for detection of a gene encoding a protein having an ability of transport of acidic amino acids or its analogue in a sodium-independent manner. It can be also used as a primer for obtaining a gene encoding the protein and the gene encoding a protein having high homology thereto. Further, it can be used for modulation of expression of a gene encoding a protein having an ability to transport acidic amino acids and its analogue in a sodium-independent manner by its anti-sense chain, etc.

It is possible to prepare the corresponding antibody using the sodium-independent transporter which transports acidic amino acids of the present invention or using a polypeptide having an immunological homology thereto. The antibody can be utilized for detection, purification, and the like. of the sodium-independent transporter which transports acidic amino acids. The antibody can be manufactured using the sodium-independent transporter which transports acidic amino acids according to the present invention, a fragment thereof, synthetic peptide having a partial sequence thereof, etc. as an antigen. Polyclonal antibody can be manufactured by a conventional method where antigen is inoculated to a host animal (such as rat and rabbit) and immune serum is recovered therefrom while monoclonal antibody can be manufactured by a conventional technique such as a hybridoma method.

The protein of the present invention has an ability of transporting acidic amino acids and its analogue in a sodium-independently manner and the ability is strongly affected in the presence of various substances. By screening a substance which inhibits or accelerates the ability, the ability of the present protein for transporting the substance can be controlled.

Accordingly, the present invention provides a method for detecting an effect of a test substance as a substrate on an ability of the protein of the present invention for transporting acidic amino acids or its analogue in a sodium-independent manner using the above-mentioned protein of the present invention.

The amino acid which is transported by the protein of the present invention is the substance essential for proliferation and growth of cells and for maintenance of life, and by controlling the uptake of such a substance into cells, proliferation, growth, etc. of cells can be controlled. Accordingly, the present invention provides a method for controlling the cell proliferation by modulating an ability of the protein for transporting the acidic amino acids and analogous substance thereto using the above-mentioned protein of the present invention, a specific antibody thereof or a function-promoting or function-suppressing substance thereof.

Gene of a fusion protein of the sodium-independent transporter AGT1 transporting the acidic amino acids with 4F2hc or rBAT according to the present invention and the expressed cell thereof can be used for an in vitro test for the efficiency of permeation of a substance at a cell membrane where AGT1 is present or at the site where the presence of AGT1 is assumed. In addition, a gene of a fusion protein of the sodium-independent transporter AGT1 transporting the acidic amino acids with 4F2hc or rBAT and the expressed cell thereof can be used for the development of a compound which efficiently permeates through a cell membrane where AGT1 is present or at the site where the presence of AGT1 is assumed. Further, a gene of a fusion protein of the sodium-independent transporter AGT1 transporting the acidic amino acids with 4F2hc or rBAT and the expressed cell thereof can be used for an in vitro test of pharmaceutical interaction at a cell membrane where AGT1 is present or at the site where the presence of AGT1 is assumed.

Accordingly, the present invention provides a method for changing the pharmacokinetics of pharmaceuticals or xenobiotics transported by the above-mentioned protein of the present invention by using the protein, a specific antibody thereof or a function-promoting or function-suppressing substance thereof, by modulating an ability of the protein for transport acidic amino acids or its analogue.

As described above, since the protein of the present invention has an ability to transport acidic amino acids or its analogue in a sodium-independent manner and this ability can be suppressed or promoted not only by the number of a protein existing in a cell, but also by the presence of various substances (in the presence of a function-suppressing substance, etc. or in the presence of a function-promoting substance, etc., respectively), the present invention provides a controlling agent for transport ability of a protein for acidic amino acids or its analogue possessed by the above-mentioned protein of the present invention which comprises the protein, a specific antibody thereof or a function-promoting substance or function-suppressing substance thereof.

Since the controlling agent for transport ability of the present invention can control the proliferation, growth, and the like. of cells, it can be used as a controlling agent for cell proliferation, and since the agent can modulate and control the pharmacokinetics of pharmaceutical, toxic substance or xenobiotics, it can be-used as a controlling agent for pharmacokinetics of pharmaceutical, toxin or xenobiotics.

By suppressing the sodium-independent transporter AGT1 of the present invention which transports acidic amino acids, the permeation of a specific compound through the cell membrane where AGT1 is expressed or through the site where AGT1 is assumed to be present can be limited. In addition, a gene of a fusion protein of the sodium-independent transporter AGT1 of the present invention transporting the acidic amino acids with 4F2hc or rBAT and its expression cell can be used for the development of a pharmaceutical (such as a specific inhibitor for AGT1) which limits the permeation of a compound transported by AGT1 through a cell membrane or the site where AGT1 is assumed to be present.

Further, in accordance with the present invention, it has been found that the protein having an amino acid sequence represented by SEQ ID NO: 3 or NO: 5 comprises an ability to promote the transfer AGT1 into a cell membrane. Accordingly, the present invention provides a promoting agent for the transfer of AGT1 into a cell membrane containing a protein having an amino acid sequence represented by SEQ ID NO: 3 or NO: 5 or a protein having an amino acid sequence where one or several amino acid(s) of the above protein is/are deleted, substituted or added.

All of the contents mentioned in the specification of the Japanese patent application No. 2002-040,608 shall be incorporated into the present specification.

EXAMPLES

The present invention will now be illustrated in more detail by way of the following Examples although those Examples do not limit the present invention.

In the following Examples, each operation was carried out, unless otherwise clearly mentioned, according to a method mentioned in "Molecular Cloning" by Sambrook, J., Fritsh, E. F. and Manitis, T. (Cold Spring Harbor Press, 1989) or according to the Directions for Use of the commercially available products when the commercially available reagents or kits are used.

Example 1

Cloning and Expression Analysis of a Sodium-Independent Transporter Which Transports Acidic Amino Acids (1) Identification of Mouse cDNA of a Sodium-Independent Transporter Which Transports Acidic Amino Acids cDNA clone corresponding to the base sequence GenBank™/EBI/DDBJ accession No. A1314100 derived from mouse analogous to rat BAT1 obtained by searching the EST (expressed sequence tag) database using a base sequence of a translation region of rat BAT1 (Chairoungdua, et al., *J. Biol. Chem.*, 274: 28845-28848, 1999) was purchased from IMAGE (Integrated and Molecular Analysis of Genomes and their Expression) (IMAGE clone I. D.: 1907807) and its fragment (1.8-kb) cleaved by a restriction enzyme XhoI was labeled with $^{32}$P-dCTP and used as a probe whereby a mouse kidney cDNA library was screened.

The cDNA library was prepared from poly(A)$^+$RNA derived from mouse kidney using a kit for the synthesis of cDNA (trade name: Superscript Choice System, manufactured by Gibco) and incorporated into a site of phage vector λZipLox (manufactured by Gibco) cleaved by a restriction enzyme EcoRI. Hybridization by a probe labeled with $^{32}$P-dCTP was carried out for one night in a solution for hybridization of 37° C. and the filter membrane was washed with 0.1×SSC/0.1% SDS at 37° C. With regard to the solution for hybridization, a buffer of pH 6.5 containing 5×SSC, 3× Denhard's solution, 0.2% SDS, 10% dextran sulfate, 50% formamide, 0.01% Abtiform B (trade name; Sigma) (antifoaming agent), 0.2 mg/ml salmon sperm-modified DNA, 2.5 mM sodium pyrophosphate and 25 mM MES was used. The cDNA portion of λZipLox phage into which cDNA was incorporated was incorporated into a plasmid pZL1. The resulting cDNA-inserted fragment of clone was further incorporated into an NotI-cleaved site of a plasmid pcDNA 3.1 (Invitrogen).

A base sequence for the full-length cDNA was determined by a dye terminator cycle sequencing method (Applied Biosystems) using a synthetic primer for the determination of base sequence. Further, a base sequence of cDNA was analyzed by a conventional method and translation region of cDNA and amino acid sequence of the protein encoded thereby were determined.

Those sequences are represented in SEQ ID NO: 1 of the Sequence Listing which will be shown later.

AGT1 comprised a 48% homology to a mouse transporter Asc-2 corresponding to a neutral amino acid transport system asc. Further, AGT1 comprised a 35% homology to a rat transporter LAT1 and 37% to LAT2 corresponding to a neutral amino acid transport system L, 37% homology to a rat transporter y$^+$LAT1 and 36% to a human transporter y$^+$LAT2 corresponding to neutral and basic amino acid transport system y$^+$L. Furthermore, AGT1 comprised a 37% homology to a mouse transporter Asc-1 corresponding to a neutral amino acid transport system asc, 37% to a mouse transporter xCT corresponding to a cystine and acidic amino acid transport system $x_c$ and 36% to a rat transporter BAT1 corresponding to a cystine, neutral and basic amino acid transport system $b^{0,+}$. Still further, Asc-2 comprised a 30% homology to a mouse and human transporter CAT1 to 4 corresponding to a basic amino acid transport system y$^+$.

Figure 1:
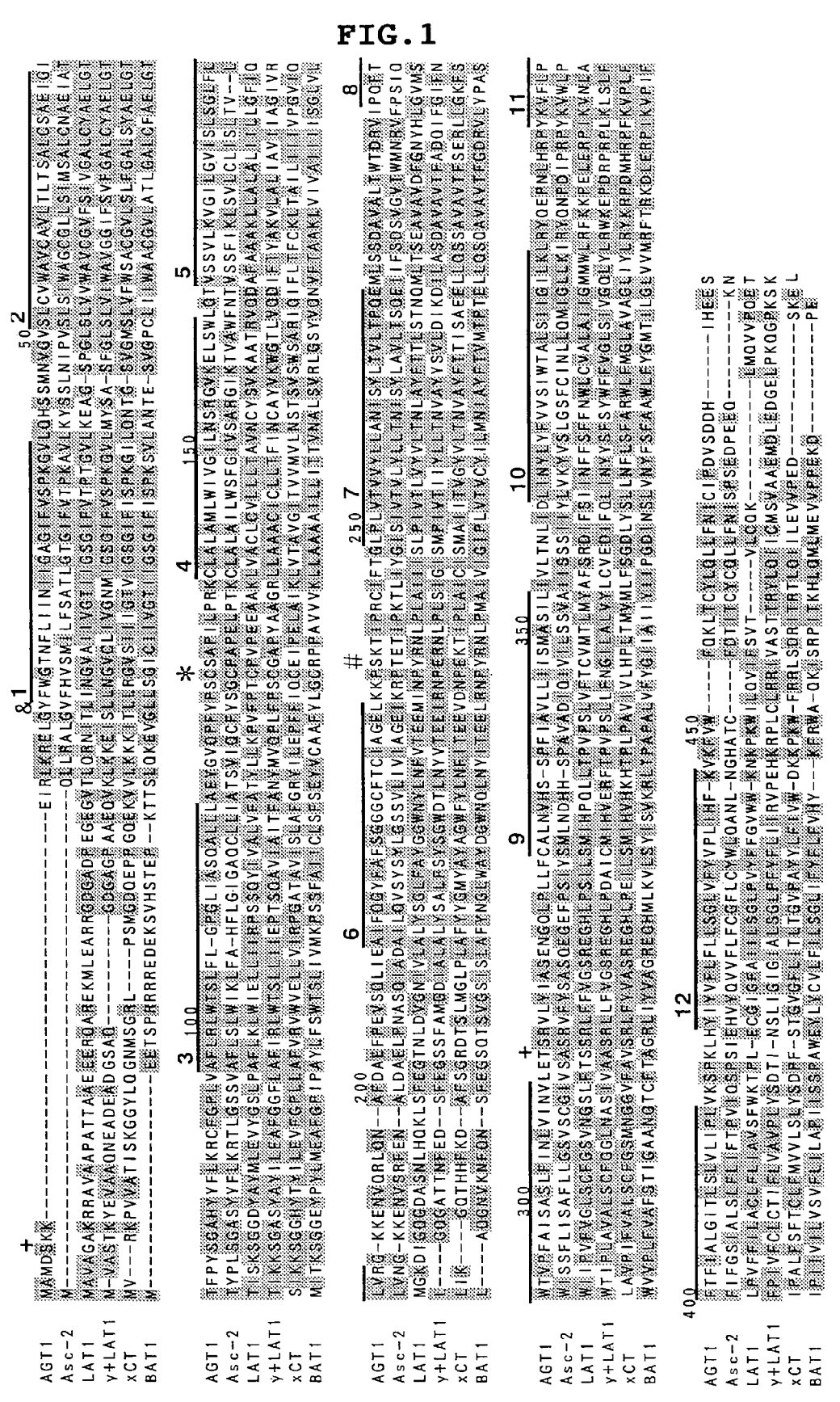

Comparison of AGT1 with mouse Asc-2, rat LAT1, rat y$^+$LAT1, mouse xCT and rat BAT1 in terms of amino acid sequences is shown in FIG. 1.

When an amino acid sequence of AGT1 was analyzed by an SOSU1 algorithm (Hirokawa, T., et al., *Bioinformatics*, volume 14, page 378 (1998)), 12 membrane-spanning domains were assumed as shown in FIG. 1. In the third hydrophilic loop, conversed cysteine residues were present among Asc-2, LAT1, Asc-2, y+LAT1, xCT and BAT1. It is assumed that, via the cysteine residue, AGT1 is binded to unknown factor via a disulfide bond. In addition, there were sites believed to be a camp-dependent phosphorylation site in the eighth hydrophilic loop, C-kinase-dependant phoshorylation sites in an N-terminal intracellular region and the sixth hydrophilic loop and a tyrosine phosphorylation site in an N-terminal intracellular region respectively.

(2) Expression of AGT1 Gene in Various Tissues of Mouse (Analysis by Northern Blotting)

cDNA fragments corresponding to 43rd to 1836th base pair of AGT1 gene were amplified by a PCR, labeled with $^{32}$P-dCTP and using as a probe, a northern blotting was carried out in the following manner to RNA extracted from various tissues of mouse. 3 μg of poly(A)$^+$RNA was subjected to an electrophoresis using 1% agarose/formaldehyde gel and then transferred to a nitrocellulose filter. The filter was subjected to a hybridization for one night using a hybridization solution containing Asc-2 cDNA fragments labeled with $^{32}$P-dCTP. The filter was washed at 65° C. with 0.1×SSC containing 0.1% SDS.

Figure 2:
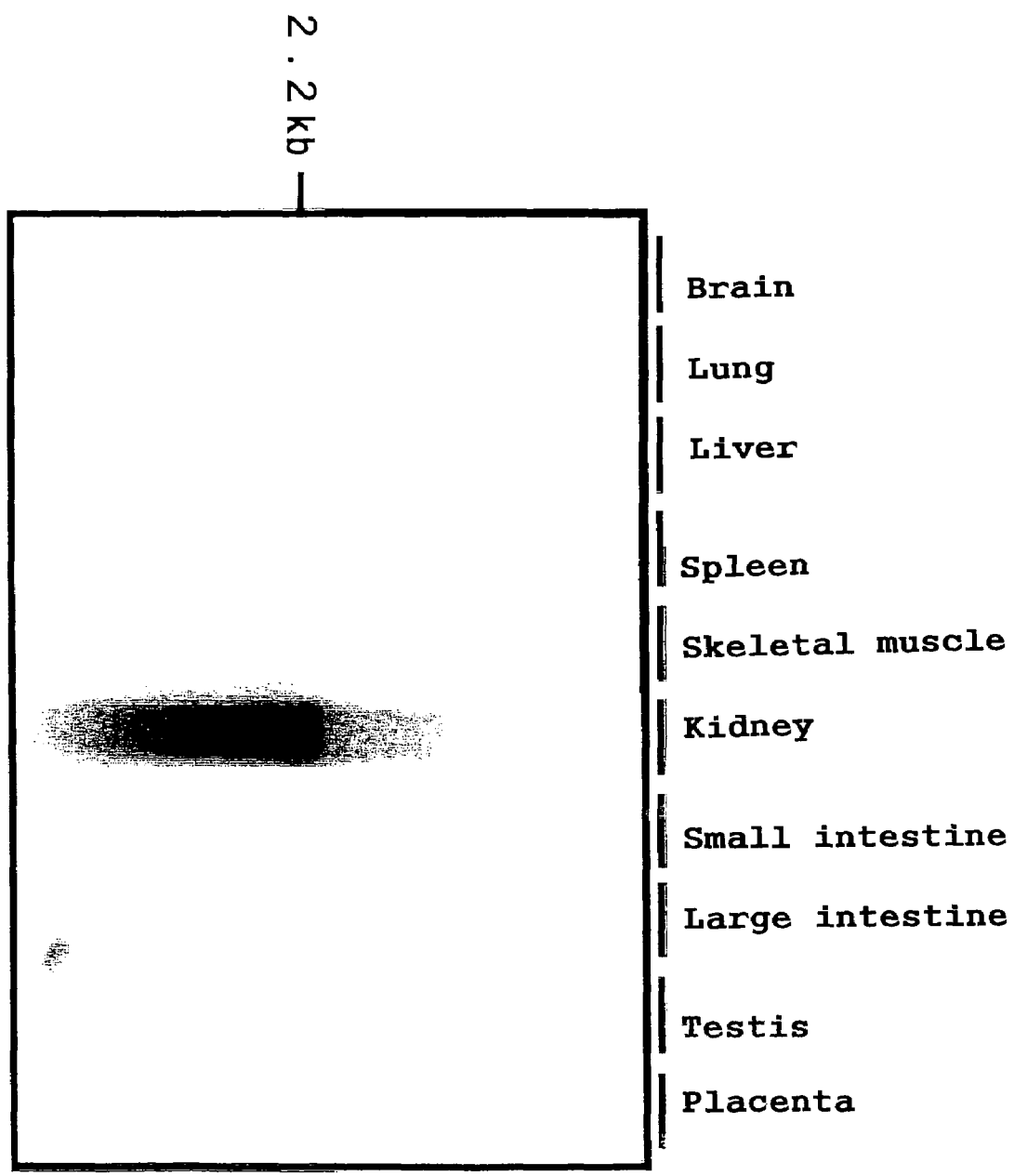
FIG. 2 is a photographic picture as a substitute for drawing which shows the result of analysis of expression of AGT1 gene mRNA in various organ tissues of mouse by means of a northern blotting.

As a result of the northern blotting (FIG. 2), a band was detected at about 2.2 kb in the kidney.

(3) Expression of AGT1 Protein in the Mouse Kidney

A specific antibody to synthetic oligopeptide (CIPDVSD-DHIHEES) (mentioned in SEQ ID NO: 7 of Sequence Listing) corresponding to 465-478 of mouse AGT1 was prepared according to a method of Altman, et al. (Altman, et al., *Proc. Natl. Acad. Sci. USA*, volume 81, pages 2176-2180, 1984).

Membrane fraction of mouse kidney was prepared according to a method of Thorens, et al. (Thorens, et al., *Cell*, volume 55, pages 281-290, 1988). The protein sample was treated at 100° C. for 5 minutes in the presence (under a reducing condition) or absence (under a non-reducing condition) of 5% 2-mercaptoethanol, subjected to electrophoresis by an SDS-polyacrylamide gel, blotted to Hybond-P PVDV transfer membrane and treated with an anti-AGT1 antiserum (1:10,000).

Figure 3:
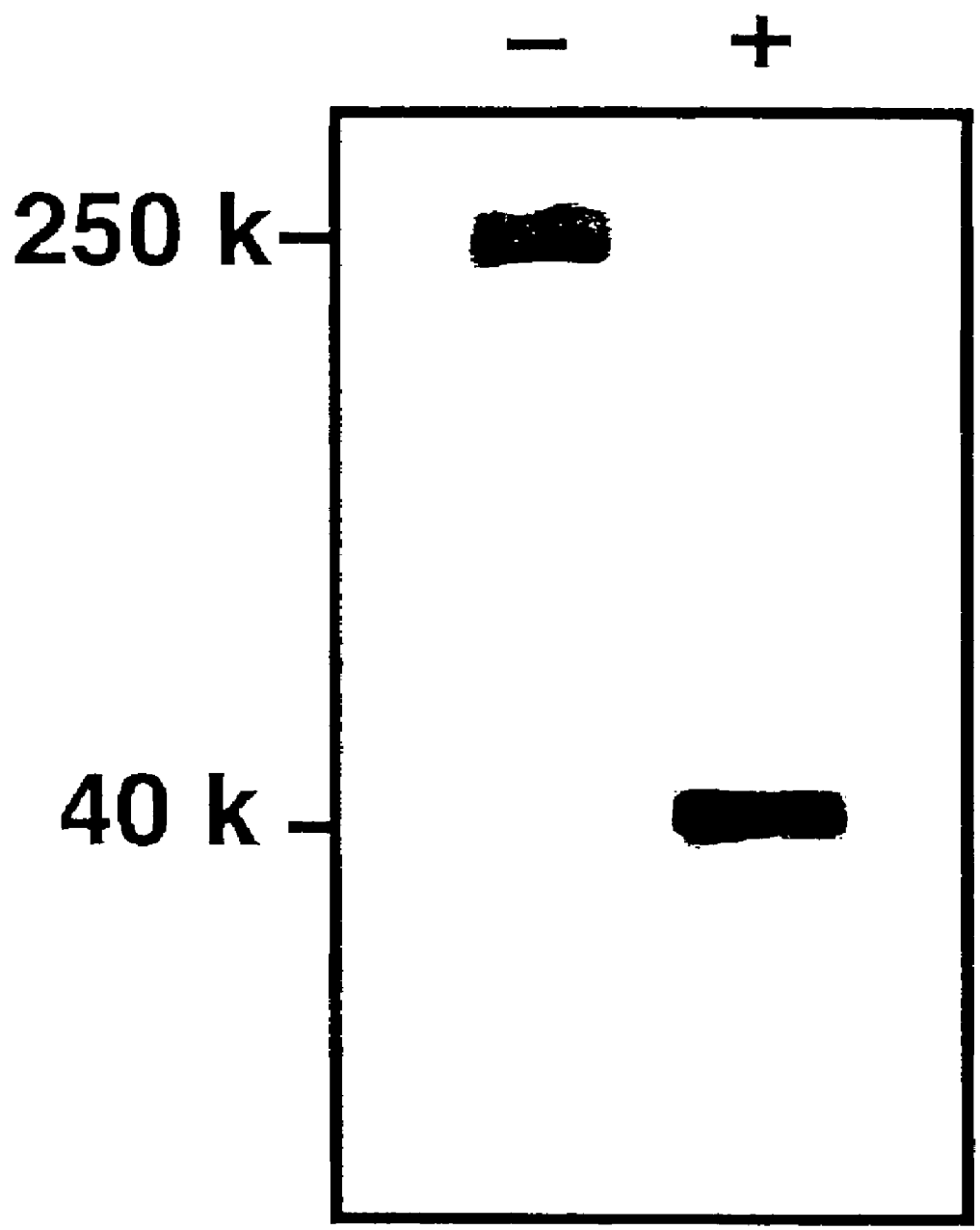
FIG. 3 is a photograph as a substitute for drawing which shows the result of the western blotting analysis by an anti-AGT1 antibody. It was carried out under a non-reducing condition (−) and a reducing condition (+) in a mouse kidney membrane specimen.

As a result, in the mouse kidney, a band was detected near 250 kDa under a non-reducing condition by an anti-AGT1 antibody as shown in FIG. 3. Under a reducing condition, a band was detected near 40 kDa. From those results, it is suggested that AGT1 is binded to some protein by a disulfide bond.

(4) Immunohistological Analysis of AGT1 Protein in the Mouse Kidney

According to a conventional method, a mouse kidney paraffin slice was treated with an anti-AGT1 antiserum (1:1,000) and colored with diaminobenzidine. Further, with an object of investigating the specificity of color development, an experiment of Treating with an antio-AGT-1 antiserum (1:1,000) in the presence of 50 μg/ml of an antigen peptide was also carried out.

Figure 4:
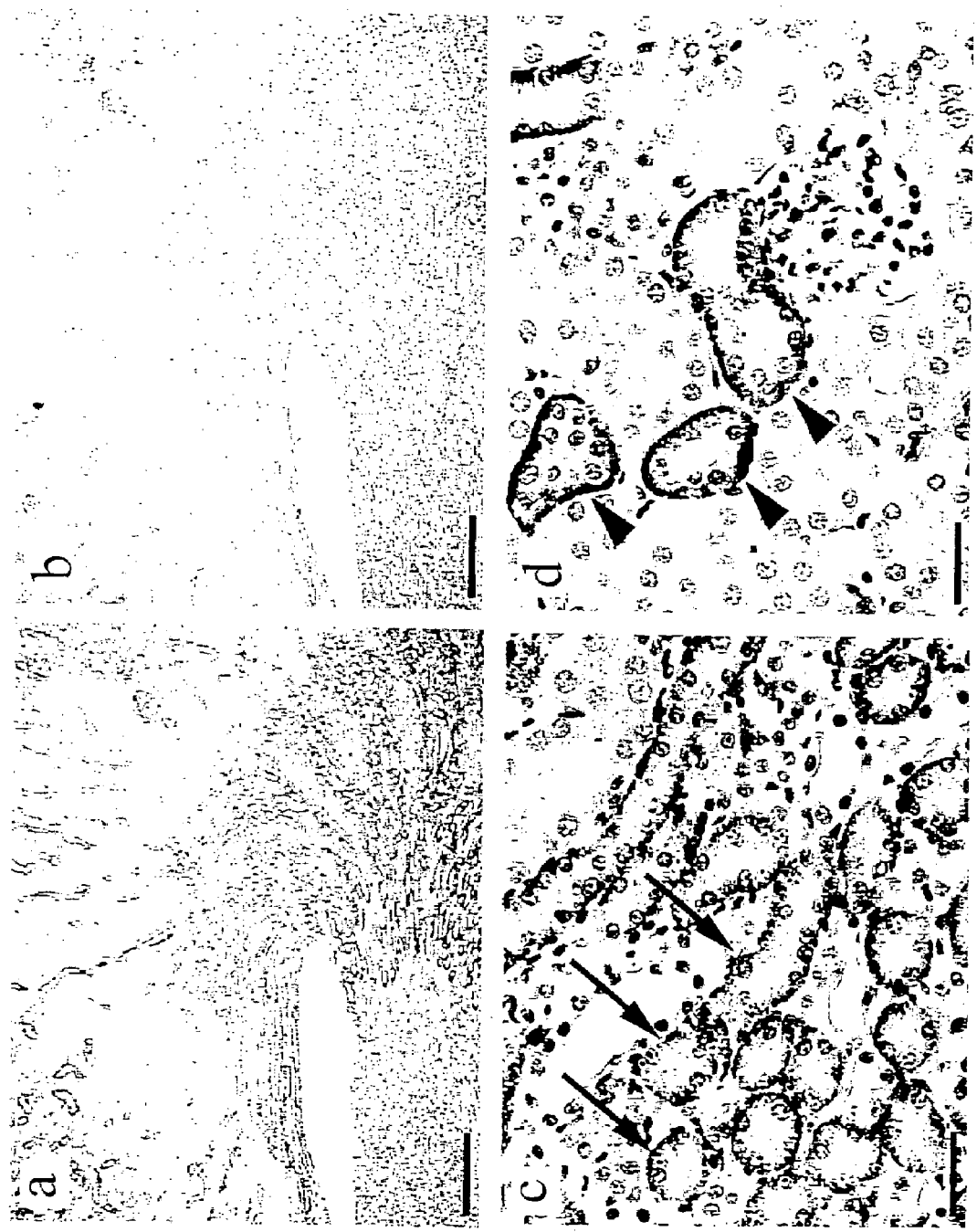
FIG. 4 is a photograph as a substitute for drawing which shows the result of immunohistological analysis of AGT1 by an anti-AGT1 antibody in a mouse kidney. a: slightly magnified image. Stainings are observed in proximal tubule of outer layer of medulla and in distal tubule of cortex. b: absorption experiment by antigen peptide. Stainings observed in "a" disappeared and specificity of staining was shown. c and d: highly magnified images of proximal tubule (c) and distal tubule (d). Stainings are observed in the side of basolateral membrane.

As a result, in the mouse kidney, stainings were noted in proximal tubule of outer layer of medulla and in distal tubule of cortex as shown in FIG. 4a. As the stainings were not detected when an anti-AGT1 antiserum was made to act in the presence of an antigen peptide, the specificity in staining was shown (FIG. 4b). Further, when an observation was conducted with highly magnified, it was clarified that AGT1 protein was present in basolateral membrane of proximal tubule (FIG. 4c) and distal tubule (FIG. 4d).

Example 2

Figure 5:
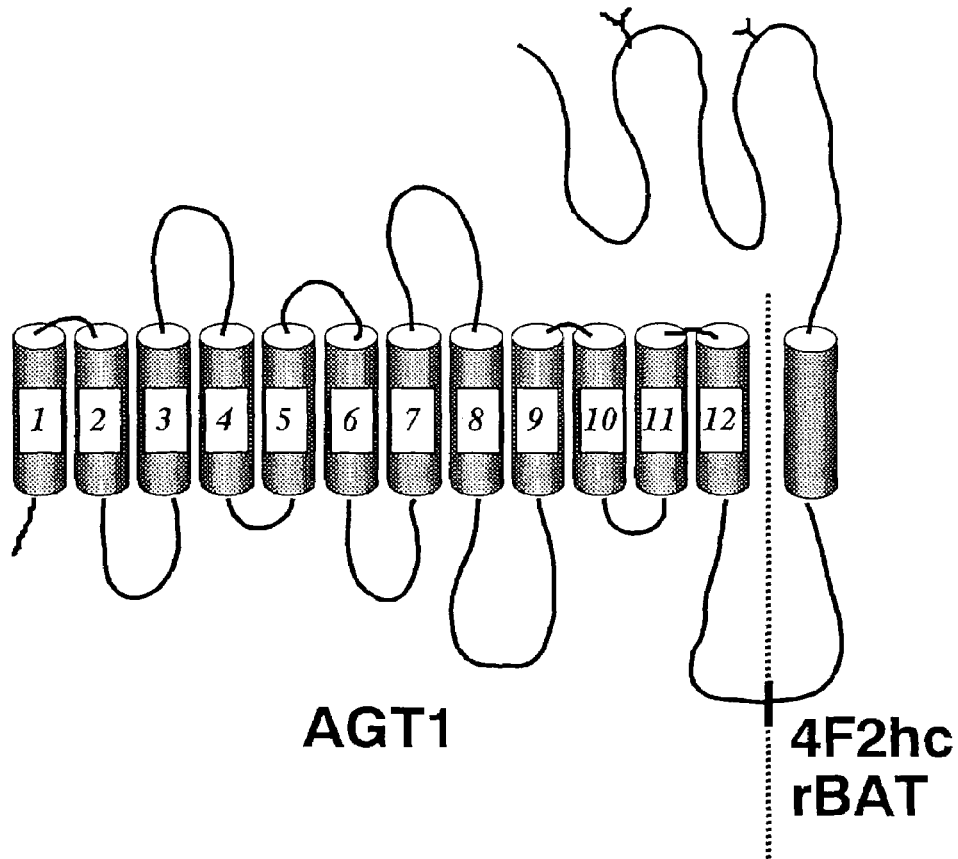
FIG. 5 is a schematic drawing of a fusion protein prepared by connecting AGT1 with 4F2hc or rBAT. Amino acid sequences and gene base sequences of the connection parts of AGT1-4F2hc fusion protein and AGT1-rBAT fusion protein are shown below in FIG. 5 (SEQ ID NOS 19-22).

Preparation of a Fusion Protein of Sodium-Independent Transporter AGT1 Transporting Acidic Amino Acids With 4F2hc or With rBAT and Analysis of Its Function (1) Preparation of a Fusion Protein of Sodium-Independent Transporter AGT1 Transporting Acidic Amino Acids with 4F2hc or rBAT In order to prepare a fusion protein of AGT1 with rBAT (AGT1-rBAT), a PCR was carried out using synthetic oligo-DNA primers 5'-GCGCGAAGCTTACCTATAGGCA-GAAACATTC-3' (in which, to a sequence corresponding to 4th to 23rd base pair of AGT1 cDNA were added a sequence corresponding to cleaved site with HindIII and GCGC at 5'-side; mentioned in SEQ ID NO: 8 of the Sequence Listing) and 5'-ATATGCGGCCGCACTTTCTTCATGTATGTGGT-3' (in which, to a sequence corresponding to 1473rd to 1492nd base pair of AGT1 cDNA were added a sequence corresponding to the cleaved site with NotI and ATAT at 5'-side; mentioned in SEQ ID NO: 9 of the Sequence Listing) where AGT1 cDNA was used as a template. The resulting PCR product was cleaved with HindIII and NotI and ligated to HindIII and NotI sites of mammalian cell expression vector pcDNA3.1(+) (Invitrogen). Further, a PCR was carried out using a synthetic oligo-DNA primers 5'-ATATGCGGCCG-CAGATGAGGACAAAGGCAAGAG-3' (in which, to a sequence corresponding to the base pair immediately after translation initiation codon ATG of mouse rBAT to 21st as shown in SEQ ID NO: 6 were added a sequence corresponding to a site cleaved by NotI and ATAT at 5'-side; mentioned in SEQ ID NO: 10 in the Sequence Listing) and 5'-GCGCGCTCTAGAAATGCTTTAGTATTTG-GCATAATC-3' (in which, to a sequence of 2228th to 2251st base pair of mouse rBAT as shown by SEQ ID NO: 6 were added a sequence corresponding to a site cleaved with XbaI and GCGC at 5'-side; mentioned in SEQ ID NO: 11 in the Sequence Listing) where rBAT cDNA was used as a template. The resulting PCR product was cleaved with NotI and XbaI and ligated to NotI and XbaI sites of the mammalian cell expression vector pcDNA3.1(+) into which the above-mentioned AGT1 PCR product was incorporated to prepare cDNA encoding a fusion protein of AGT1 with rBAT (FIG. 5).

In order to prepare a fusion protein of AGT1 with 4F2hc (AGT1-4F2hc), a PCR was carried out using synthetic oligo-DNA primers 5'-GCGCGAAGCTTACCTATAGGCA-GAAACATTC-3' (in which, to a sequence corresponding to 4th to 23rd base pair of AGT1 cDNA were added a sequence corresponding to a site cleaved by HindIII and GCGC at 5'-side; mentioned in SEQ ID NO: 8 of the Sequence Listing) and 5'-ATATGCGGCCGCACTTTCTTCATGTATGTGGT-3' (in which, to a sequence corresponding to 1473rd to 1492nd base pair of AGT1 cDNA were added a sequence corresponding to a site cleaved by NotI and ATAT at 5'-side; mentioned in SEQ ID NO: 9 of the Sequence Listing) where AGT1 cDNA was used as a template. The resulting PCR product was cleaved with HindIII and NotI and ligated to HindIII and NotI sites of mammalian cell expression vector pcDNA3.1(+) (Invitrogen). Further, a PCR was carried out using synthetic oligo-DNA primers 5'-ATATGCGGCCGCAAGCCAGGA-CACCGAAGTGGA-3' (in which, to a sequence corresponding to the base pair immediately after translation initiation codon ATG of mouse 4F2hc to 21st as shown in SEQ ID NO: 4 were added a sequence corresponding to a site cleaved by NotI and ATAT at 5'-side; mentioned in SEQ ID NO: 12 in the Sequence Listing) and 55'-GCGCTCTAGACATGAG-GCAGGGGTGATGTTTT-3' (in which, to a sequence corresponding to 1820th to 1838th base pair of mouse 4F2hc shown in SEQ ID NO: 4 were added a sequence corresponding to a site cleaved by XbaI and GCGC at 5'-side; mentioned in SEQ ID NO: 13 of the Sequence Listing) where 4F2hc cDNA was used as a template. The resulting PCR product was cleaved with NotI and XbaI and ligated to NotI and XbaI sites of mammalian cell expression vector pcDNA3.1 (+) into which the above-mentioned AGT 1 PCR product was incorporated to give cDNA encoding a fusion protein of AGT 1 with 4F2hc (FIG. 5).

(2) Expression of a Function of a Fusion Protein of a Sodium-Independent Transporter AGT1 Transporting Acidic Amino Acids With 4F2hc or rBAT Comparisons were conducted for the uptake of aspartic acid when mouse AGT1 gene cRNA was expressed in the oocyte, when mouse AGT1 gene cRNA and mouse 4F2hc gene cRNA were expressed in the oocyte and when a fusion protein of ACT1 with 4F2hc or rBAT was expressed in the oocyte.

25 ng of mouse 4F2hc gene cRNA, 25 ng of AGT1 gene cRNA, 12.5 ng of AGT1 gene cRNA/12.5 ng of mouse 4F2hc gene cRNA, 25 ng of AGT1-4F2hc fusion protein gene cRNA or 25 ng of AGT1-rBAT fusion protein gene cRNA was injected into the oocyte to express and incubation was conducted for 3 days.

With regard to the oocyte into which mouse 4F2hc gene cRNA, AGT1 gene cRNA, AGT1 gene ckNA/mouse 4F2hc gene cRNA, AGT1-4F2hc fusion protein gene cRNA or AGT1-rBAT fusion protein gene cRNA was injected, experiments for the uptake of a substrate was carried out using aspartic acid as a substrate according to a method of Kanai, et al. (Kanai and Hediger, *Nature*, volume 360, pages 467-471, 1992) as follows. The oocyte were allowed to stand for 30 minutes in a sodium-free uptake solution (100 mM choline chloride, 2 mM potassium chloride, 1.8 mM calcium chloride, 1 mM magnesium chloride and 5 mM HEPES; pH 7.4) containing $^{14}$C-aspartic acid (20 μM) as a substrate and an uptake rate of the substrate was measured by the count of radioactivity incorporated into the cells.

Figure 6:
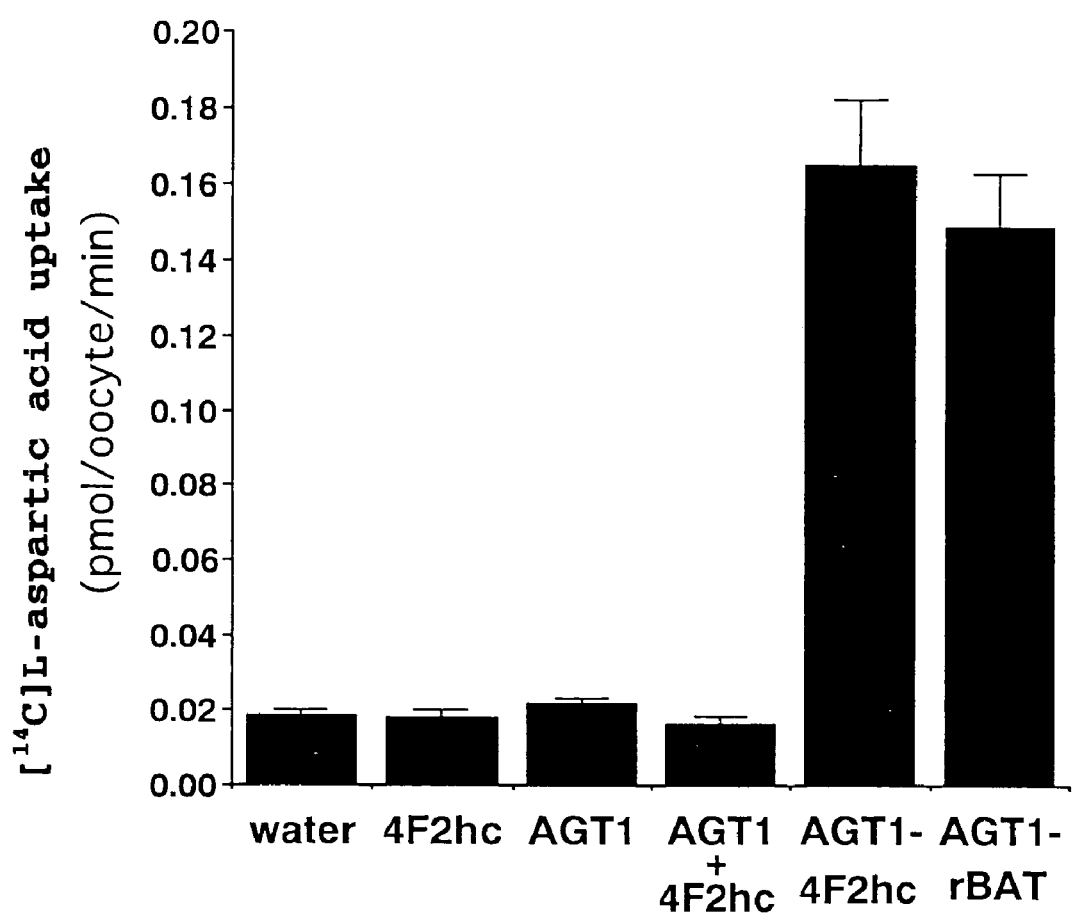
FIG. 6 shows the result of experiment of the uptake of aspartic acid by an oocyte into which mouse 4F2hc gene cRNA, AGT1 gene cRNA, AGT1 gene cRNA/mouse 4F2hc gene cRNA, AGT1-4F2hc fusion protein gene cRNA or AGT1-rBAT fusion protein gene cRNA is injected.

As a result (FIG. 6), the levels of the uptake of aspartic acid in the oocyte where only 4F2hc was expressed, the oocyte where only AGT1 was expressed and the oocyte where both AGT1 and 4F2hc were co-expressed were similar to that in the control oocyte into which water was injected, while a higher uptake of aspartic acid was noted in the oocyte where AGT 1-rBAT or AGT 1-4F2hc was expressed.

It was investigated that rBAT or 4F2hc cannot be a direct cofactor of AGT1 using COS-7 cells. According to a method mentioned in Mizoguchi, et al., *Kidney Int.*, 59: 1821-1833, 2001, plasmid DNA (each 1 mg) containing AGT1 cDNA, rBAT cDNA or 4F2hc cDNA was introduced into COS-7 cells using LIPOFECTAMINE 2000 Reagent (Life Technologies). After the introduction, the cells were incubated for two days in a 24-well plate and the uptake $^{14}$C-aspartic acid (20 μM) was measured. Measurement of the uptake was conducted according to a method of Mizoguchi, et al., *Kidney Int.*, 59: 1821-1833, 2001, in which it was started by removing the culture liquid and adding Dulbecco's PBS (manufactured by Gibco) containing $^{14}$C-aspartic acid, and completed by removing it and washing with ice-cooled Dulbecco's PBS. After the washing, it was dissolved with 0.1N NaOH and radioactivity was measured by a liquid scintillation counter.

Figure 7:
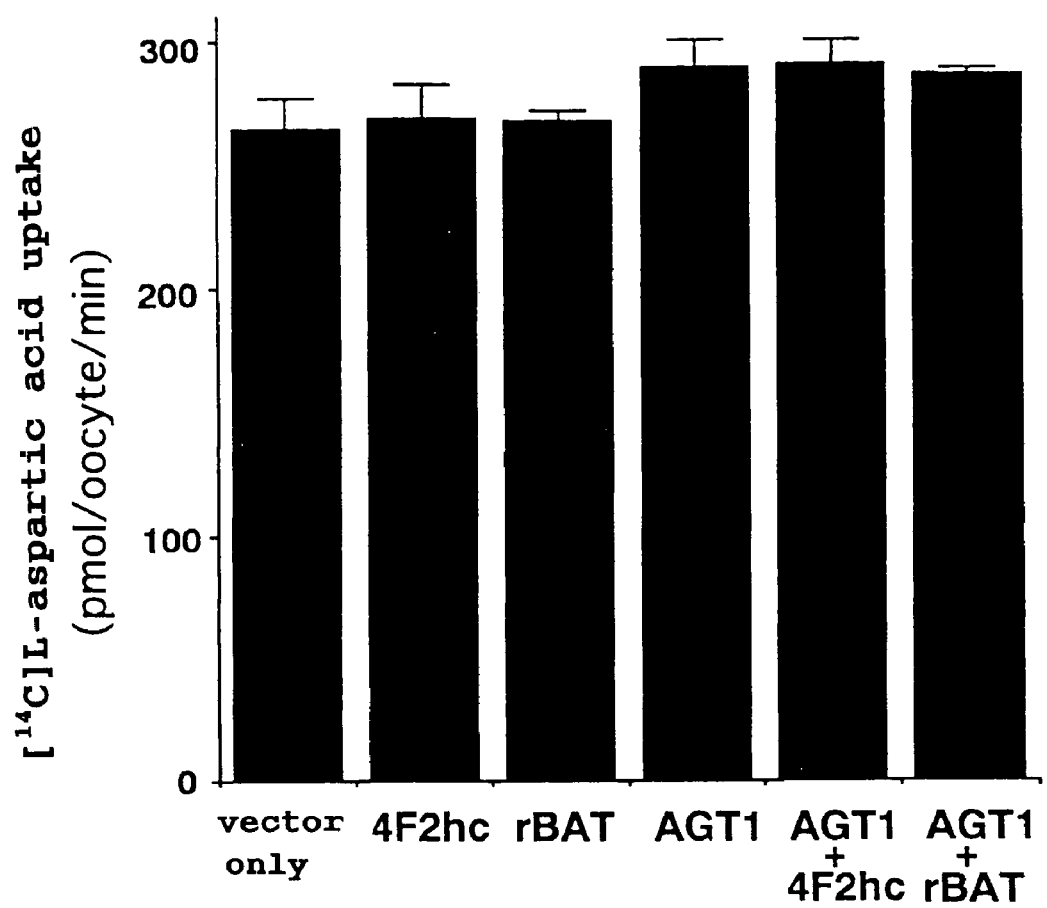
FIG. 7 shows the result of experiment of the uptake of aspartic acid by COS-7 cells into which mouse 4F2hc gene, mouse rBAT gene, AGT1 gene, AGT1 gene/mouse 4F2hc gene or AGT1 gene/mouse rBAT gene is injected.

As a result (FIG. 7), the levels of the uptake of aspartic acid in the oocyte where only 4F2hc was expressed, the oocyte where only rBAT was expressed, the oocyte where only AGT1 was expressed, the oocyte where both AGT1 and 4F2hc were co-expressed and the oocyte where both AGT1 and rBAT were co-expressed were similar to that the control oocyte into which a pcDNA 3.1 plasmid containing no inserted cDNA whereby it was confirmed that rBAT or 4F2hc was not a direct cofactor for AGT1.

(3) Identification of Expression of a Fusion Protein of Sodium-Independent Transporter AGT1 Transporting Acidic Amino Acids With 4F2hc (AGT1-4F2hc) in Oocyte Cell Membrane by a Immunofluorescence Analysis Whether the fact that when AGT1 was expressed in the oocyte, no function was observed while a fusion protein of AGT1 with 4F2hc (AGT1-4F2hc) showed a functional activity is due to the fact that AGT1 is not transported to a cell membrane while AGT1-4F2hc is transported to a cell membrane or not was investigated by a immunofluorescence analysis.

25 ng of AGT1 gene cRNA or 25 ng of the cRNA of a gene of a fusion protein of AGT1 with 4F2hc(AGT1-4F2hc) was injected into the oocyte to express, incubated for 3 days and, the oocyte was fixed in a 4% paraformaldehyde-phosphate buffer and prepared a paraffin section (3 μm) according to a conventional method. After removing the paraffin, the section was subjected to a blocking with 5% goat serum in 0.05M Tris buffer in a physiological saline containing 0.1% Tween 20 and treated with an affinity-purified anti-Asc-2 antibody or an affinity-purified anti-4F2hc antibody (Fukasawa, et al., *J. Biol. Chem.*, 275: 9690-9698, 2000). Then, the section was treated with Alexa Fluor 488-labeled goat anti-rabbit IgG (Molecular Probe, Inc.), washed with 0.05M Tris buffer in physiological saline containing 0.1% Tween 20 and observed with Olympus Fluoview (FV500) confocal laser microscope (Olympus). Excitation was effected with argon laser at 488 nm and fluorescence from Alexa Fluor 488 was detected using a BA505IF filter.

Figure 8:
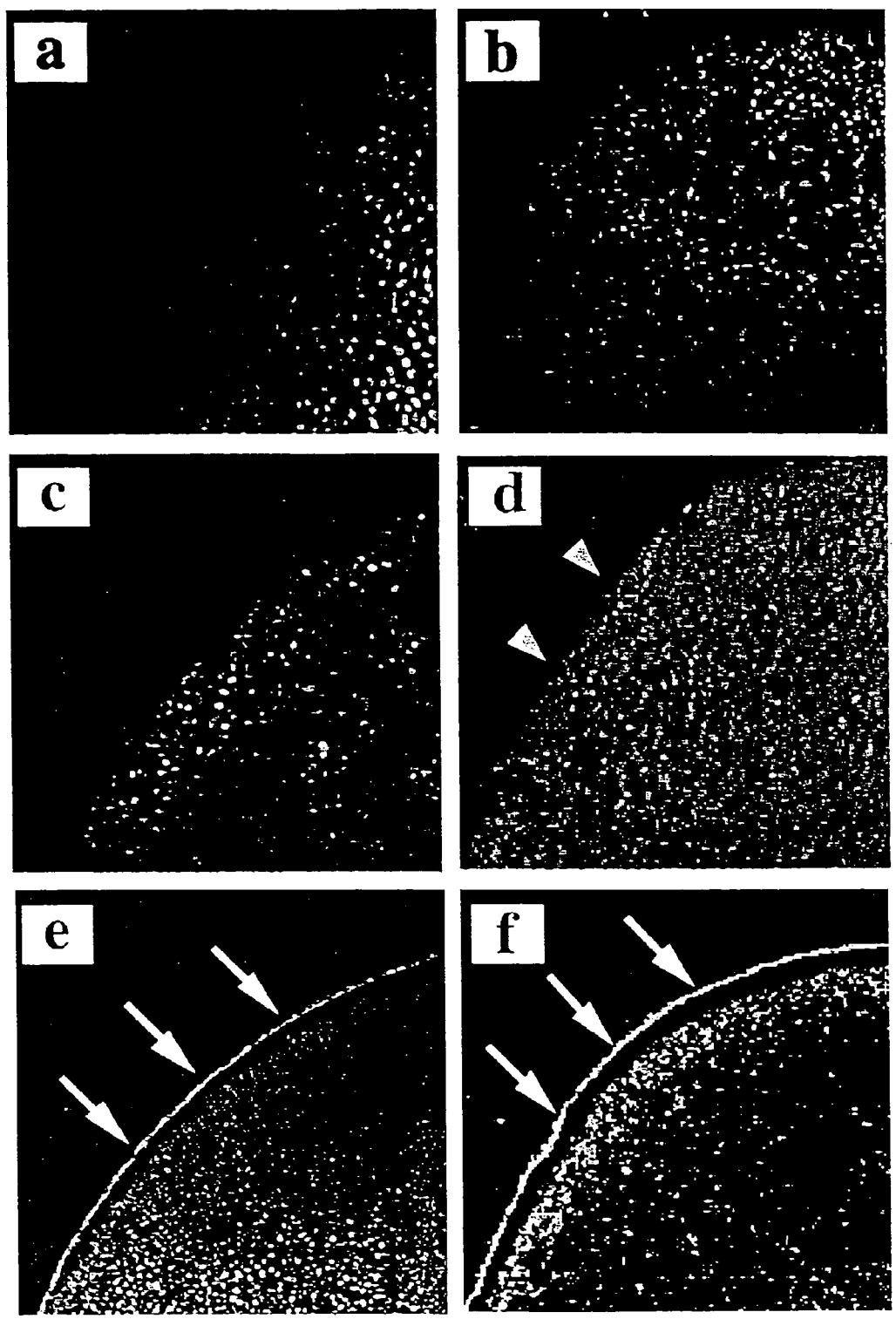
FIG. 8 is a drawing which shows the result of investigating the expression of a fusion protein of AGT1 with 4F2hc (AGT1-4F2hc) in an oocyte cell membrane by a immunofluorescence analysis. As controls, investigations by a immunofluorescence analysis were carried out using an anti-4F2hc antibody (a, c and e) or an anti-AGT1 antibody in the oocyte into which water was injected (a and b), the oocyte into which AGT1 gene cRNA was injected and expressed (c and d) and the oocyte into which a fusion protein (AGT1-4F2hc) gene cRNA of AGT1 with 4F2hc was injected and expressed (e and f).

As a result (FIG. 8), in the oocyte in which AGT1 was expressed, an AGT1 protein detected in an anti-AGT1 antibody was not present in a cell membrane but remained inside the cell membrane (FIG. 8d), while in an oocyte in which a fusion protein of AGT1 with 4F2hc(AGT1-4F2hc) was expressed, an AGT1-4F2hc fusion protein expressed in a cell membrane was detected in both anti-4F2hc antibody (FIG. 8e) and anti-AGT1 antibody (FIG. 8f). In the control oocyte into which water was injected, no specific color development by anti-4F2hc antibody (FIG. 8a) or anti-AGT1 antibody (FIG. 8b) was observed. Accordingly, it was proven that the fact that no function was observed when AGT1 was expressed in the oocyte while a fusion protein of AGT1 with 4F2hc (AGT1-4F2hc) showed a functional activity is due to the fact that AGT1 is not transported to a cell membrane by itself, while its fusion protein with 4F2hc (AGT1-4F2hc) is transported to a cell membrane.

(4) Salt-Dependency of Transport Activity of AGT1

In an uptake experiment of aspartic acid by the oocyte into which a cRNA of a gene of a fusion protein of AGT1 with 4F2hc or with rBAT (AGT1-4F2hc or AGT1-rBAT) was injected, influence of salt added to the medium was investigated.

An uptake experiment of aspartic acid was carried out according to the method mentioned in the above Example 2(2) using an oocyte into which a cRNA of a gene of a fusion protein of AGT1 with 4F2hc or with rBAT (AGT1-4F2hc or AGT1-rBAT) was injected. With regard to the uptake solution, a standard uptake solution (100 mM of choline chloride was exchanged with 100 mM sodium chloride) was used instead of a sodium-free uptake solution when the effect of sodium ion was investigated. A gluconic acid uptake solution (100 mM sodium chloride was exchanged with 100 mM sodium gluconate) was used instead of a standard uptake solution when the effect of chlorine ion was investigated.

Figure 9:
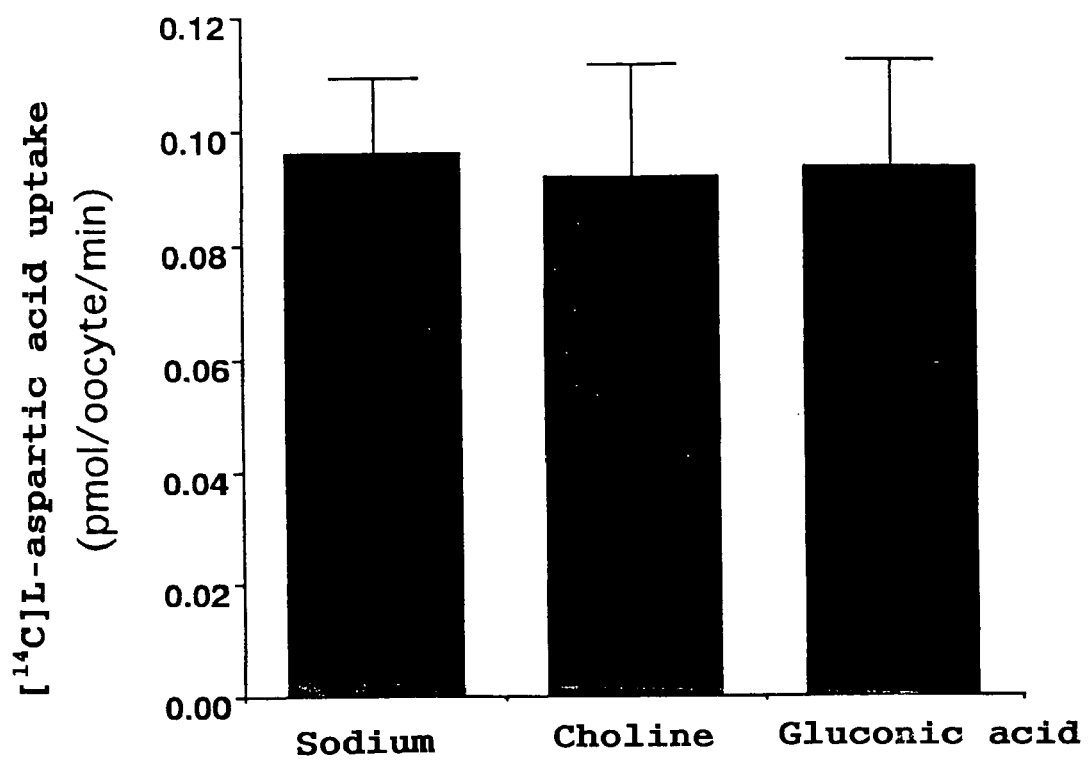
FIG. 9 shows the result of investigating the influence of added salt in an experiment of the uptake of aspartic acid by an oocyte into which a fusion protein (AGT1-4F2hc) gene cRNA of AGT1 with 4F2hc was injected.

As a result (FIG. 9), even when extracellular choline was exchanged with sodium or even when extracellular chlorine was exchanged with gluconate ion, it did not affect the uptake of aspartic acid at all. From the above, it was noted that Asc-2 is a transporter which acts independently on sodium ion and chlorine ion.

(5) Michaelis-Menten Kinetic Analysis of AGT1

A Michaelis-Menten kinetic analysis of sodium-independent transporter AGT1 which transports acidic amino acids was carried out. The Michaelis-Menten kinetic analysis was conducted by investigating the change in the ratio of uptake of aspartic acid by the difference in the substrate aspartic acid concentration.

Figure 10:
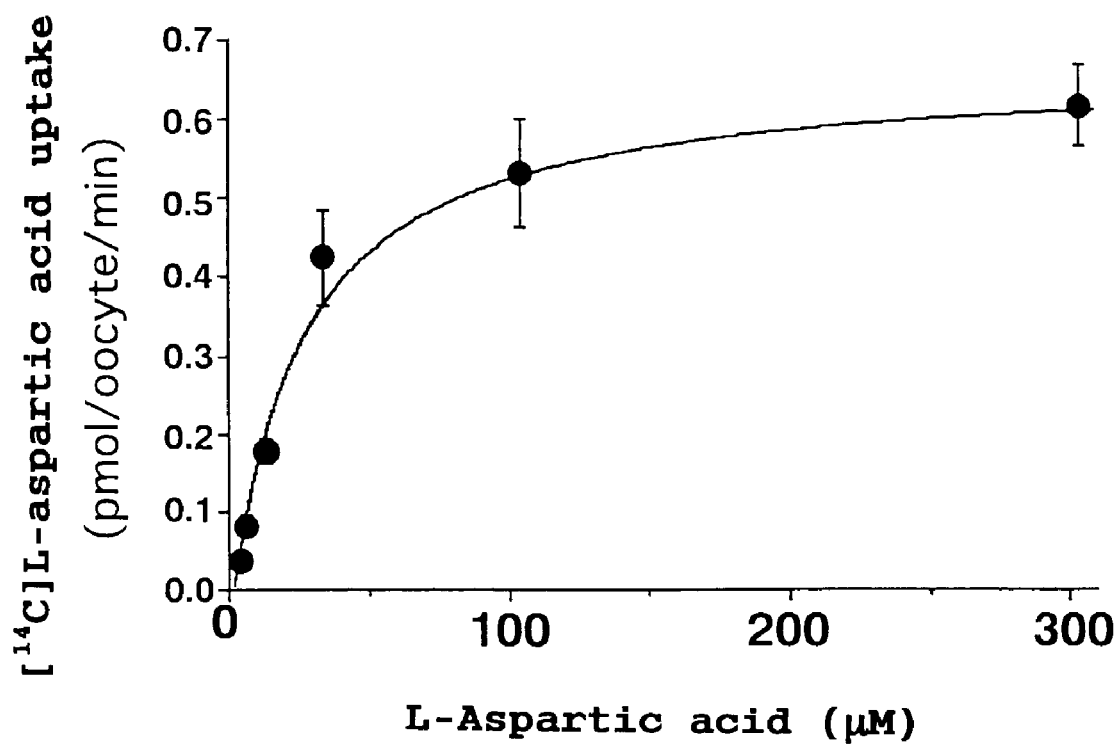
FIG. 10 shows the result of investigating the influence of the concentration of substrate aspartic acid in an experiment of the uptake of aspartic acid by an oocyte into which a fusion protein (AGT1-4F2hc) gene cRNA of AGT1 with 4F2hc was injected.

The aspartic acid uptake experiment was carried according to the method mentioned in the above Example 2(2) using the oocyte into which a cRNA of a gene of a fusion protein of AGT1 with 4F2hc or with rBAT (AGT1-4F2hc or AGT1-rBAT) was injected. As a result (FIG. 10), the Km value of aspartic acid transport by AGT1-4F2hc was 25.5±5.9 µM (mean value ± standard error). The Km value of aspartic acid transport by AGT1-rBAT was 20.1±6.1 µM.

The Michaelis-Menten kinetic analysis was similarly carried out in a fusion protein of AGT1 with 4F2hc (AGT1-4F2hc) in glutamic acid and Km value and Vmax value were calculated. Result of the above is shown in the following Table 1.

TABLE 1

Km values and Vmax values of substrate amino acid

| Amino Acid | $Km^a$ (µM) | $Vmax^b$ |
|---|---|---|
| L-Aspartic acid | 25.5 ± 5.9 | (1.00) |
| L-Glutamic acid | 21.8 ± 6.5 | 0.63 ± 0.10 |

[a, b]V max value of L-glutamic acid is shown by the ratio to Vmax value of L-aspartic acid. Both Km and Vmax values are represented by mean value ± standard error.

(6) Substrate Selectivity of AGT1 (Inhibition Experiment Using Added Amino Acid and Its Analogue)

In an uptake experiment of aspartic acid by an oocyte into which a cRNA of a gene of a fusion protein of AGT1 with 4F2hc (AGT1-4F2hc) was injected, the effect of addition of various amino acids and their analogues on the system was investigated.

An aspartic acid uptake experiment was carried out according to the method mentioned in the above Example 2(2) using an oocyte into which a cRNA of a gene of a fusion protein of AGT1 with 4F2hc (AGT1-4F2hc) was injected. However, a sodium-free uptake solution was used and the uptake $^{14}$C-aspartic acid (20 µM) was measured in the presence and absence of 2 mM of various compounds (non-labeled).

Figure 11:
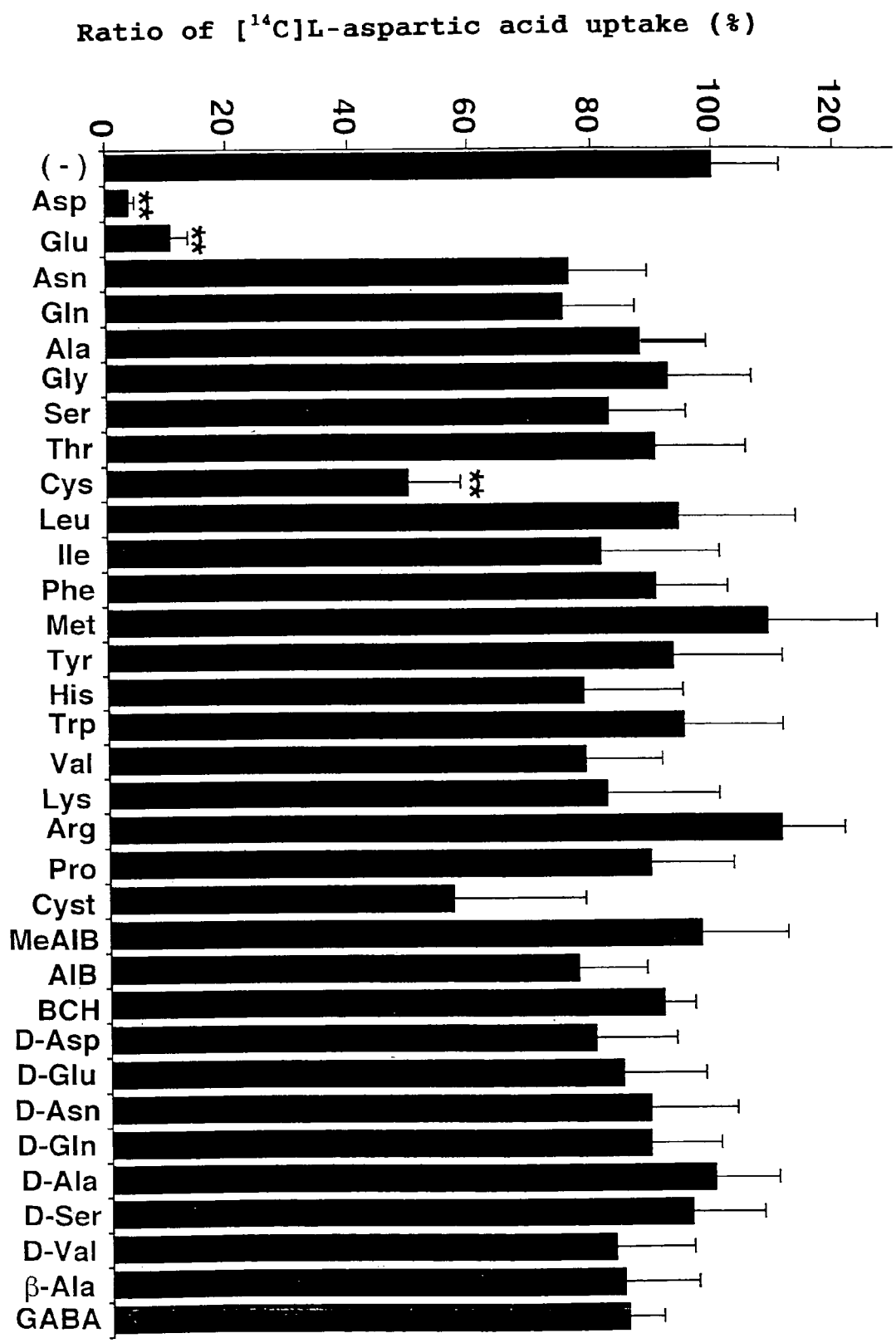
FIG. 11 shows the result of investigating the influence of addition of various amino acids and analogous compounds on a system in an experiment of the uptake of aspartic acid by an oocyte into which a fusion protein (AGT1-4F2hc) gene cRNA of AGT1 with 4F2hc was injected.

As a result (FIG. 11), in aspartic acid, glutamic acid and cysteine, a significant cis-inhibiting effect was observed. Basic amino acids, neutral amino acids except cysteine, cystine, 2-amino-2-norbornane-carboxylic acid (BCH) which is a transport system L-specific inhibitor, γ-aminoisobutyric acid, α-aminomethylisobutyric acid, D-aspartic acid and D-glutamic acid did no affect the uptake of $^{14}$C-aspartic acid mediated by AGT1-4F2hc (FIG. 11).

In an oocyte into which cRNA of a gene of a fusion protein of AGT1 with rBAT (AGT1-rBAT) were injected together, the effect of adding various amino acids and their analogues on the system was also investigated in an aspartic acid uptake experiment by an oocyte in a similar manner as in the case of AGT1-4F2hc.

As a result, in the case of AGT1-rBAT, the same result as in the case of AGT1-4F2hc was obtained, and in the case of a fusion protein of AGT1 with 4F2hc or with rBAT (AGT1-4F2hc or AGT1-rBAT), the 4F2hc or rBAT moiety did not affect the characteristic of substrate-binding site and, with regard to the information concerning the substrate selectivity obtained in a fusion protein, the AGT1 itself also reflects the transport characteristic.

In the substances analogous to acidic amino acids, threo-β-hydroxyaspartate (THA), L-serine-O-sulfate (SOS), L-cysteine sulfate and L-cysteate strongly inhibited the uptake of $^{14}$C-aspartic acid mediated by AGT1.

Figure 12:
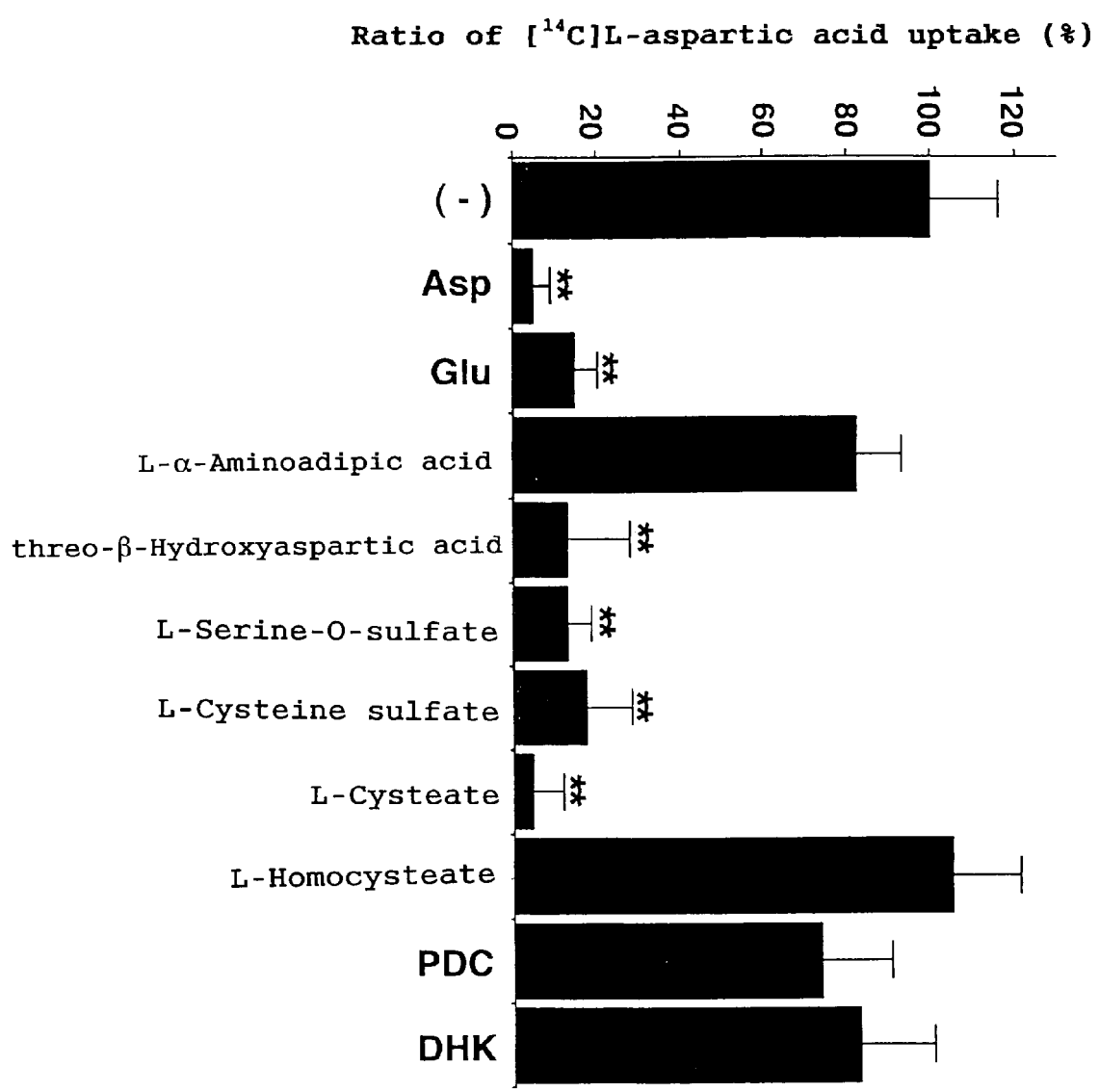
FIG. 12 shows the result of investigating the influence of addition of various acidic amino acids and analogous compounds on a system in an experiment of the uptake of aspartic acid by an oocyte into which a fusion protein (AGT1-4F2hc) gene cRNA of AGT1 with 4F2hc was injected.

On the contrary, in the case of L-α-aminoadipate, L-homocysteate, L-trans-pyrrolidine-2,4-dicarboxylate (PDC) and dihydrokainate (DHK), no inhibition effect on the uptake of $^{14}$C-aspartic acid mediated by AGT1 was observed (FIG. 12).

(7) Substrate Selectivity of AGT1 (Uptake Experiment Using Various Amino Acids and Their Analogues as Substrates)

Various kinds of amino acids and their analogues were used as substrates and uptake by an oocyte into which a cRNA of a gene of a fusion protein of AGT1 with 4F2hc (AGT1-4F2hc) was injected was investigated.

The uptake experiment of various amino acids and their analogues was carried out according to the method mentioned in the above-mentioned Example 2(2) using an oocyte into which a cRNA of a gene of a fusion protein of AGT1 with 4F2hc (AGT1-4F2hc) was injected. With regard to a substrate, various compounds which were labeled with radioactivity were used instead of $^{14}$C-aspartic acid.

As a result, when L-glutamic acid ($^{14}$C compound) was used as a substrate in addition to L-aspartic acid ($^{14}$C compound) (FIG. 13), a substantial uptake into the oocyte was observed.

INDUSTRIAL APPLICABILITY

The sodium-independent transporter of the present invention which transports acidic amino acids and a gene thereof enables an in vitro investigation of transport of acidic amino acids and amino acid analogues including xenobiotics at the site where the transporter is expressed, and based on which, also enables an in vitro assumption of pharmacokinetic of these compounds. Further, the present invention is useful for the development of pharmaceutical which permeates efficiently through a site where the transporter is expressed. Furthermore, by modulating an ability to transport acidic amino acids and its analogue possessed by the transporter, the invention can be utilized for the development of a method for controlling a cell proliferation.

---

The invention claimed is:

1. A method for determining the transport of a test substance in a sodium-independent manner by a protein having the amino acid sequence of SEQ ID NO: 1, which comprises the steps of: (a) preparing cells expressing said protein, (b) contacting said cells with the test substance, and (c) determining if the test substance is transported into the cells.

2. A method for screening a substance which modulates the ability of the protein having the amino acid sequence of SEQ ID NO: 1, to transport acidic amino acids, which comprises the steps of: (a) preparing cells expressing said protein, (b) contacting said cells with the substance and acidic amino acids, and (c) determining if the test substance modulates the ability to transport acidic amino acids into the cells.

* * * * *